US006586173B2

(12) United States Patent
Tang

(10) Patent No.: US 6,586,173 B2
(45) Date of Patent: Jul. 1, 2003

(54) METHODS FOR THE DETECTION OF AMINO ACID DECARBOXYLASES

(75) Inventor: Liang Tang, Fort Collins, CO (US)

(73) Assignee: Heska Corporation, Fort Collins, CO (US)

( * ) Notice: Subject to any disclaimer, the term of this patent is extended or adjusted under 35 U.S.C. 154(b) by 0 days.

(21) Appl. No.: 09/777,558

(22) Filed: Feb. 5, 2001

(65) Prior Publication Data

US 2002/0081313 A1 Jun. 27, 2002

(30) Foreign Application Priority Data

Aug. 5, 1999 (WO) .............................. PCT/US99/17858

(51) Int. Cl.$^7$ ............................................... C12Q 1/00
(52) U.S. Cl. ......................................................... 435/4
(58) Field of Search ............................................. 435/4

(56) References Cited

U.S. PATENT DOCUMENTS 4,183,858 A 1/1980 Metcalf et al.

FOREIGN PATENT DOCUMENTS

WO WO 98/30593 7/1998

OTHER PUBLICATIONS

Barboni et al., 1981, Biochemical and Biophysical Research Communications, 99:2, pp. 576–583.
Berger et al., 1984, In Vitro, 20:12, pp. 959–974.
Berry et al., 1996, Neurochemical Research, 21:9, pp. 1075–1087.
Black et al., 1986, Biochimica et Biophysica Acta, 870, pp. 31–40.
Bray et al., 1986, The EMBO Journal, 5:9, 99. 2305–2311.
Charteris et al., 1975, Analytical Biochemistry, 66, pp. 365–371.
Clark et al., 1986, Developmental Biology, 114, pp. 141–150.
Clark et al., 1978, Molec. gen. Genet., 162, pp. 287–297.
Cooper et al., 1991, The Biochemical Basis of Neuropharmacology, 6th Ed., Oxford Univ. Press, Oxford, NY, pp. 285–337.
Cumming et al., 1997, Journal of Cerebral Blood Flow and Metabolism, 17, pp. 1254–1260.
Davenport et al., 1984, Insect Biochem., 14:2, pp. 135–143.
Ferdig et al., 1996, Insect Molecular Biology, 5:2, pp. 199–126.
Gietz et al., 1985, Developmental Biology, 107, pp. 142–155.
Han et al., 1996, Journal of Neurochemistry, pp. 501–510.
Harris et al., 1992, J. Insect Physiol., 38:1, pp. 29–35.
Hiruma et al., 1995, Developmental Biology, 169, pp. 195–209.
Hiruma et al., 1990, Developmental Biology, 138, pp. 214–224.
Hodgetts et al., 1986, Progress in Developmental Biology, Part A, pp. 221–234.
Hodgetts et al., 1995, Development, 121, pp. 3913–3922.
Hong et al., 1993, Experimental Parasitology, 76, pp. 127–133.
Jabai et al., 1997, Académie des sciences, 320, pp. 349–358.
Konrad et al., 1987, Developmental Biology, 122, pp. 172–185.
Kozánek et al., 1988, Endocrinological Frontiers in Physiological insect Ecology, Ed. by F. Sehnal et al., Wroclaw Technical University Press, Wroclaw, pp. 161–167.
Kozánek et al., 1986, Acta ent. bohemoslov, 83, pp. 171–178.
Lovenberg et al., 1962, The Journal of Biological Chemistry, 237:1, pp. 89–93.
Lovenberg et al., 1963, Archives of Biochemistry and Biophysics, 103, pp. 9–14.
Maneckjee et al., 1983, Biochemistry, 22, pp. 6058–6063.
Mantzouridis et al., 1997, Gene, 204, pp. 85–89.
Maras et al., 1991, Eur. J. Biochem., 201, pp. 385–391.
Marsh et al., 1985, Mol Gen Genet, 198, pp. 393–403.
Marsh et al., 1980, Developmental Biology, 80, pp. 379–387.
Marsh et al., 1986, Genetics 114, pp. 453–467.
Mastick et al., 1992, Molecular and Cellular Biology, 12:12, pp. 5659–5666.
Nappi et al., 1992, Comp. Biochem. Physiol., 101B:3, pp. 453–460.
Rauschenbach et al., 1997, Insect Biochem. Molec. Biol., 27:8/9, pp. 729/734.
Richer et al., 1992, Experimental Parasitology, 75, pp. 213–222.
Scholnick et al., 1986, Science, 234, pp. 998–1002.
Sourkes, T.L., 1987, Methods in Enzymology, 142, pp. 170–178.
Spencer et al., 1983, Can. J. Biochem. Cell Biol., 61, pp. 818–825.
Sugiura et al., 1997, Psychopharmacology, 133, pp. 249–255.

(List continued on next page.)

Primary Examiner—Mark Navarro
(74) Attorney, Agent, or Firm—Heska Corporation

(57) ABSTRACT

The present invention relates to parasitic helminth aromatic amino acid decarboxylase proteins; to parasitic helminth aromatic amino acid decarboxylase nucleic acid molecules, including those that encode such aromatic amino acid decarboxylase proteins; to antibodies raised against such aromatic amino acid decarboxylase proteins; and to compounds that inhibit parasitic helminth aromatic amino acid decarboxylase activity. The present invention also includes methods to obtain such proteins, nucleic acid molecules, antibodies, and inhibitory compounds. Also included in the present invention are therapeutic compositions comprising such proteins, nucleic acid molecules, antibodies and/or inhibitory compounds as well as the use of such therapeutic compositions to protect animals from diseases caused by filariids. The present invention also includes a method for detecting the presence of amino acid decarboxylases.

7 Claims, 1 Drawing Sheet

OTHER PUBLICATIONS

Swiderski et al., 1986, *Progress in Developmental Biology*, Part A, pp. 235–238.

Swiderski et al., 1986, *Molecular and Cellular Biology*, 6:12, pp. 4433–4439.

Tempel et al., 1984, *Proc. Natl. Acad. Sci. USA*, 81, pp. 3577–3581.

Voltattorni et al., 1987, *Methods in Enzymology*, 142, pp. 179–187.

Walter et al., 1996, *Archives of Insect Biochemistry and Physiology*, 31, pp. 219–233.

Wang et al., 1995, *Developmental Biology*, 168, pp. 598–612.

Wright, T.R.F., 1996, *The Journal of Heredity*, 87:3, pp. 175–190.

Zhu et al., 1995, *Gen. Pharmac.*, 26:4, pp. 681–696.

Zimmerman et al., 1976, *Analytical Biochemistry*, 70, pp. 258–262.

Zimmerman et al., 1977, *Analytical Biochemistry*, 78, pp. 47–51.

Wilson et al., GenBank Access No. Z49068, submitted Apr. 19, 1995, XP–002129673.

Wilson et al., 1994, *Nature*, vol. 368, pp. 32–39.

METHODS FOR THE DETECTION OF AMINO ACID DECARBOXYLASES

CROSS-REFERENCE TO RELATED APPLICATIONS

This application claims priority to international PCT Application No. PCT/US99/17858, filed Aug. 5, 1999.

FIELD OF THE INVENTION

The present invention relates to parasitic helminth aromatic amino acid decarboxylase (ADC) nucleic acid molecules, proteins encoded by such nucleic acid molecules, antibodies raised against such proteins, compounds capable of inhibiting the function of such proteins and methods to identify such inhibitors. The present invention also includes therapeutic compositions comprising such nucleic acid molecules, proteins, antibodies, and/or inhibitors, as well as their use to protect animals from diseases caused by parasitic helminths. The present invention also includes a method for detecting the presence of amino acid decarboxylases.

BACKGROUND OF THE INVENTION

Parasitic helminth infections in animals, including humans, are typically treated by chemical drugs. One disadvantage with chemical drugs is that they must be administered often. For example, dogs susceptible to heartworm are typically treated monthly. Repeated administration of drugs, however, often leads to the development of resistant helminth strains that no longer respond to treatment. Furthermore, many of the chemical drugs cause harmful side effects in the animals being treated, and as larger doses become required due to the build up of resistance, the side effects become even greater. Moreover, a number of drugs only treat symptoms of a parasitic disease but are unable to prevent infection by the parasitic helminth.

An alternative method to prevent parasitic helminth infection includes administering a vaccine against a parasitic helminth. Although many investigators have tried to develop vaccines based on specific antigens, it is well understood that the ability of an antigen to stimulate antibody production does not necessarily correlate with the ability of the antigen to stimulate an immune response capable of protecting an animal from infection, particularly in the case of parasitic helminths. Although a number of antigens have been identified in several parasitic helminths, including proteases and macromolecules demonstrating protease-like activity, (See, for example, Lustigman, 1995, *Antimicrobial Agents and Chemother.*, 39(9): 1913–1919; Mehta, 1992, *Mol. Biochem. Parasitol.*, 53:1–16; Richer et al., 1992, *Exper. Parasitol.*, 75:213–222; Tripp et al., U.S. Pat. No. 5,569,603) there is yet to be a commercially available vaccine developed for any parasitic helminth.

As an example of the complexity of parasitic helminths, the life cycle of *Dirofilaria immitis*, the filariid nematode that causes heartworm, includes a variety of life forms, each of which presents different targets, and challenges, for immunization. In a mosquito, *D. immitis* microfilariae go through two larval stages (L1 and L2) and become mature third stage larvae (L3), which can then be transmitted back to the dog when the mosquito takes a blood meal. In a dog, the L3 molt to the fourth larval stage (L4), and subsequently to the fifth stage, or immature adults. The immature adults migrate to the heart and pulmonary arteries, where they mature to adult heartworms. Adult heartworms are quite large and preferentially inhabit the heart and pulmonary arteries of an animal. Sexually mature adults, after mating, produce microfilariae which traverse capillary beds and circulate in the vascular system of the dog. In particular, heartworm is a major problem in dogs, which typically do not develop immunity upon infection (i.e., dogs can become reinfected even after being cured by chemotherapy). In addition, heartworm infection has been reported in cats, ferrets, and humans.

The mechanisms and regulatory pathways involved in the development of helminths are not clear. For example, it has been shown in the free living nematode, *Caenorhabditis elegans* (*C. elegans*), that the development of the larvae is regulated by environmental signals through chemosensory neurons. Blockage of signal transmission affects the development of the nematode (Bargmann, et al., 1991, *Science*, 251, 1243–1246). Many neuron-related genes have been identified in *C. elegans*. Mutation of the genes which control normal neuron function in *C. elegans* will not only affect the behavior of the nematode, but will also affect the development of the larvae and egg laying of mutated female worms. In parasitic nematodes such as *D. immitis*, very little is known about mechanisms involved in the migration, signal transmission and the developmental regulation of the parasites. However, host and tissue specificities in parasite infections suggest that parasitic nematodes might also need correct environmental signals for development.

There has been no previous report of aromatic amino acid decarboxylases (ADC) in parasitic helminths. Although three genes coding for putative aromatic amino acid decarboxylase-like proteins have been sequenced in the free-living nematode *C. elegans*, neither biochemical properties nor biological functions of these proteins have been described. An unrelated but biochemically similar molecule, dopa-decarboxylase (DOPA-DC), has been shown to be an important enzyme in catecholamine metabolism in animals. In Drosophila, studies of DOPA-DC indicate that the majority of DOPA-DC is localized in the epidermis and that the enzyme is involved in the formation of flexible cuticle during the development of larvae (see Wright, T. R. F., 1996, *Journal of Heredity*, 87:175–190). Due to the similarities in biochemical properties and in vivo expression between DOPA-DC and parasitic helminth ADC disclosed herein it is likely that parasitic helminth ADC plays a significant role in cuticle formation during parasitic helminth development and in larval survival in the hostile conditions within the host.

As such, there remains a need to identify efficacious compositions that protect animals against diseases caused by parasitic helminths such as *D. immitis*. Such compositions would preferably also protect animals from infection by such helminths.

SUMMARY OF THE INVENTION

The present invention relates to a novel product and a process to protect animals against parasitic helminth infection (e.g., prevent and/or treat such an infection). According to the present invention there are provided parasitic helminth ADC proteins (e.g. Dirofilaria and Brugia ADC proteins) and mimetopes thereof; parasitic helminth ADC nucleic acid molecules, including those that encode such proteins; antibodies raised against such ADC proteins (i.e., anti-parasitic helminth ADC antibodies); and compounds that inhibit the function of parasitic helminth ADCs (i.e. inhibitory compounds).

The present invention also includes methods to obtain and/or identify such proteins, nucleic acid molecules, antibodies and inhibitory compounds. Also included in the present invention are therapeutic compositions comprising such proteins, nucleic acid molecules, antibodies, and/or inhibitory compounds, as well as use of such therapeutic compositions to protect animals from diseases caused by parasitic helminths.

One embodiment of the present invention is an isolated nucleic acid molecule that includes a parasitic helminth aromatic amino acid decarboxylase nucleic acid molecule. Such nucleic acid molecules are referred to as ADC nucleic acid molecules. A preferred parasitic helminth nucleic acid molecule includes an isolated nucleic acid molecule selected from the group consisting of: (a) a nucleic acid molecule having at least about 50 nucleotides wherein said nucleic acid molecule hybridizes with a nucleic acid molecule selected from the group consisting of SEQ ID NO:5, SEQ ID NO:7, SEQ ID NO:9, SEQ ID NO:11, SEQ ID NO:13, SEQ ID NO:15, SEQ ID NO:16, SEQ ID NO:18, SEQ ID NO:19 and SEQ ID NO:21 under conditions that allow about 20% base pair mismatch between said isolated nucleic acid molecule and said nucleic acid molecule having said nucleic acid sequence, and (b) a nucleic acid molecule having at least about 150 nucleotides wherein said nucleic acid sequence hybridizes with a nucleic acid molecule selected from the group consisting of SEQ ID NO:5, SEQ ID NO:7, SEQ ID NO:9, SEQ ID NO:11, SEQ ID NO:13, SEQ ID NO:15, SEQ ID NO:16, SEQ ID NO:18, SEQ ID NO:19 and SEQ ID NO:21 under conditions that allow about 30% base pair mismatch between said isolated nucleic acid molecule and said nucleic acid molecule having said nucleic acid sequence.

Additional preferred parasitic helminth nucleic acid molecules include either a Dirofilaria ADC nucleic acid molecule, preferably a *Dirofilaria immitis* (*D. immitis*) ADC nucleic acid molecule, or a Brugia ADC nucleic acid molecule, preferably a *Brugia malayi* (*B. malayi*) ADC nucleic acid molecule. A *D. immitis* ADC nucleic acid molecule preferably includes nucleic acid sequence SEQ ID NO:5, SEQ ID NO:7, SEQ ID NO:9, SEQ ID NO:11, SEQ ID NO:13, SEQ ID NO:15, SEQ ID NO:16 and/or SEQ ID NO:18, and a *B. malayi* ADC nucleic acid molecule preferably includes nucleic acid sequence SEQ ID NO:19 and/or SEQ ID NO:21.

In one embodiment, a preferred *D. immitis* ADC nucleic acid molecule comprises a nucleic acid molecule of at least about 50 nucleotides, preferably at least about 100 nucleotides, more preferably at least about 350 nucleotides, more preferably at least about 450 nucleotides, more preferably at least about 500 nucleotides even more preferably at least about 800 nucleotides. In another embodiment, a preferred *B. malayi* nucleic acid molecule comprises a nucleic acid molecule of at least about 50 nucleotides, preferably at least about 100 nucleotides, more preferably at least about 350 nucleotides, more preferably at least about 500 nucleotides even more preferably at least about 550 nucleotides. In yet another embodiment, a preferred *D. immitis* or *B. malayi* ADC nucleic acid molecule comprises a full-length coding region which encodes a full-length ADC protein.

The present invention also relates to recombinant molecules, recombinant viruses and recombinant cells that include an isolated ADC nucleic acid molecule of the present invention. Also included are methods to produce such recombinant molecules, recombinant molecules, recombinant viruses and recombinant cells.

Another embodiment of the present invention includes a parasitic helminth ADC protein. A preferred parasitic helminth ADC protein includes an isolated protein comprising an amino acid sequence that is at least about 90% identical to an amino acid sequence selected from the group consisting of SEQ ID NO:6, SEQ ID NO:10, SEQ ID NO:14, SEQ ID NO:17, and SEQ ID NO:20 or fragments thereof having at least about 35 amino acid residues.

A preferred parasitic helminth ADC protein includes a Dirofilaria or a Brugia ADC protein. More preferred ADC proteins include *Dirofilaria immitis* or *Brugia malayi* ADC proteins (referred to herein as Di-ADC or Bm-ADC proteins respectively). A preferred Di-ADC protein comprises amino acid sequence SEQ ID NO:6, SEQ ID NO:10, SEQ ID NO:14 or SEQ ID NO:17, and a preferred Bm-ADC protein comprises amino acid sequence SEQ ID NO:20.

In one embodiment, a preferred Di-ADC protein comprises an amino acid sequence of at least about 35 amino acids in length, preferably at least about 50 amino acids in length, more preferably at least about 100 amino acids in length, more preferably at least about 200 amino acids in length, even more preferably at least about 250 amino acids in length. In yet another embodiment, a preferred Bm-ADC protein comprises an amino acid sequence of at least about 35 amino acids in length, preferably at least about 50 amino acids in length, more preferably at least about 100 amino acids in length, more preferably at least about 150 amino acids in length, even more preferably at least about 180 amino acids in length. In yet another embodiment, a preferred Di-ADC or Bm-ADC protein comprises a full-length protein, i.e., a protein encoded by a full-length coding region.

The present invention also relates to mimetopes of parasitic helminth ADC proteins. A preferred mimetope of a parasitic helminth ADC protein includes a mimetope of a Dirofilaria ADC protein or a Brugia ADC protein. The present invention further relates to isolated antibodies that selectively bind to parasitic helminth ADC proteins. A preferred antibody includes an antibody that selectively binds to either a Dirofilaria ADC protein or to a mimetope thereof. Also preferred is an antibody that selectively binds to a Brugia ADC protein or to a mimetope thereof. The present invention further relates to inhibitors of parasitic helminth ADC proteins. A preferred inhibitor of parasitic helminth ADC proteins includes an inhibitor of Dirofilaria ADC protein function or an inhibitor of Brugia ADC protein function. Also included are methods, including recombinant physical or chemical methods, to produce proteins, mimetopes, antibodies, and inhibitors of the present invention. Also included is a method to identify inhibitors of ADC activity which includes the steps of contacting an isolated filariid aromatic amino acid decarboxylase protein having an amino acid sequence selected from the group consisting of SEQ ID NO:6, SEQ ID NO:10, SEQ ID NO:14, SEQ ID NO:17, and SEQ ID NO:20 with a putative inhibitory compound under conditions in which, in the absence of said compound, said protein has aromatic amino acid decarboxylase activity; and determining if said putative inhibitory compound inhibits said activity.

Yet another embodiment of the present invention is a therapeutic composition that is capable of protecting an animal from disease caused by a parasitic helminth. Such a therapeutic composition includes one or more of the following protective compounds: a parasitic helminth ADC protein or a mimetope thereof; an isolated parasitic helminth ADC nucleic acid molecule; an isolated antibody that selectively binds to a parasitic helminth ADC protein; and/or a compound capable of inhibiting ADC function identified by its ability to inhibit parasitic helminth ADC function. A preferred therapeutic composition of the present invention also includes an excipient, an adjuvant and/or a carrier. Preferred ADC nucleic acid molecule therapeutic compositions of the present invention include genetic vaccines, recombinant virus vaccines and recombinant cell vaccines. Also included in the present invention is a method to protect an animal from disease caused by a parasitic helminth, comprising the step of administering to the animal a therapeutic composition of the present invention.

Yet another embodiment of the present invention is a method for detecting the presence of an amino acid decarboxylase, said method comprising the steps of: (a) contacting a putative amino acid decarboxylase-containing composition with a synthetic substrate to create a reaction product, wherein the synthetic substrate comprises an amino acid conjugated to a tag which produces a reference signal, where the tag is cleaved from the synthetic substrate in the presence of an amino acid decarboxylase resulting in a cleavage product which produces a cleavage signal which is different from the reference signal; and (b) observing the reaction signal produced by the reaction product and comparing the reaction signal with the reference signal and the cleavage signal. A reaction signal qualitatively equivalent to the cleavage signal indicates the presence of an amino acid decarboxylase.

DETAILED DESCRIPTION OF THE INVENTION

Figure 1:
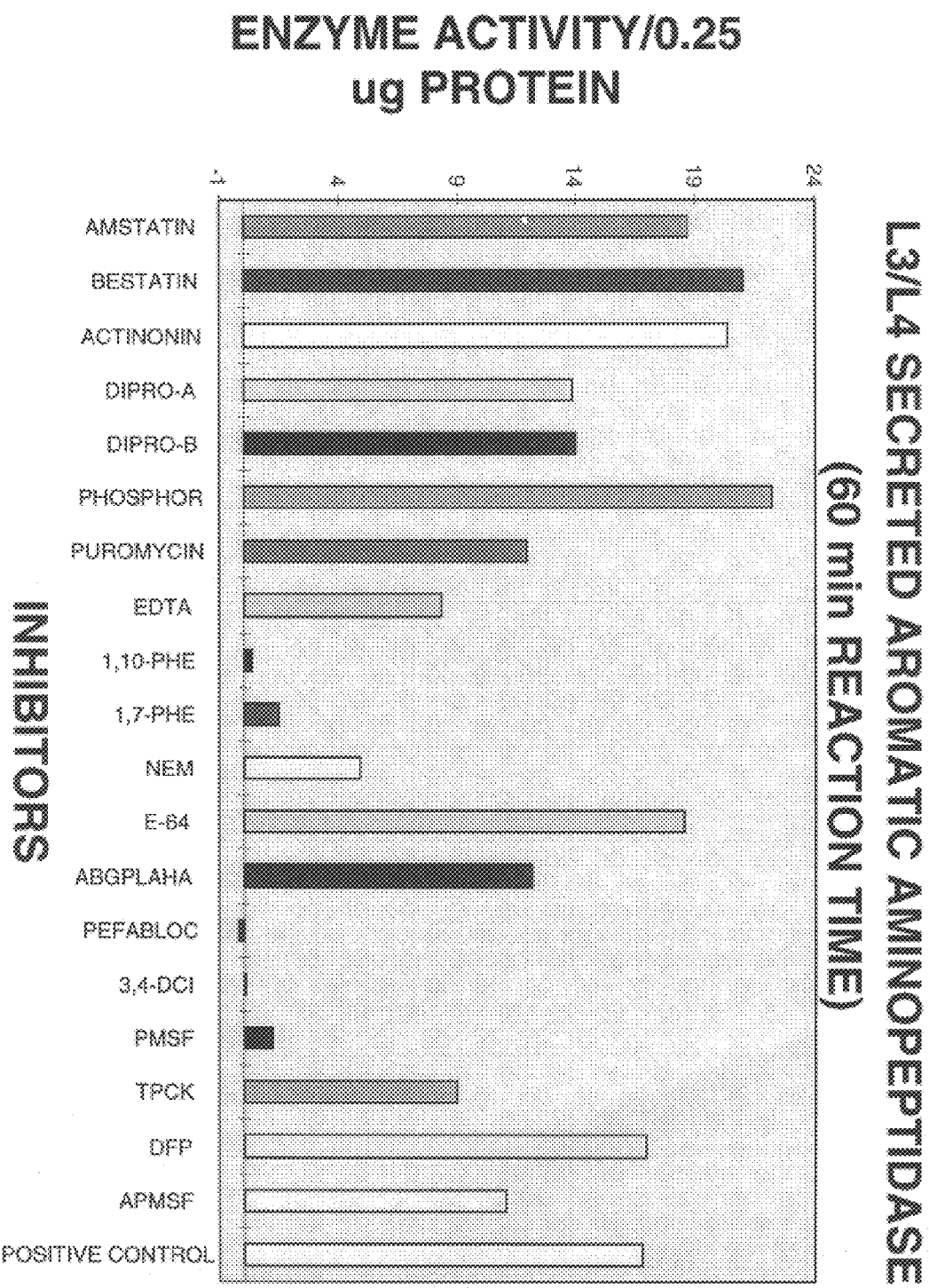
FIG. 1 illustrates the effect of 16 inhibitors upon Di-ADC purified from *D. immitis* L3/L4 ES.

The present invention provides for isolated parasitic helminth aromatic amino acid decarboxylase (ADC) proteins, isolated parasitic helminth ADC nucleic acid molecules, isolated antibodies directed against parasitic helminth ADC proteins, and compounds able to inhibit parasitic helminth aromatic amino acid decarboxylase function (i.e., inhibitory compounds). As used herein, the terms isolated parasitic helminth ADC proteins and isolated parasitic helminth ADC nucleic acid molecules refer to ADC proteins and ADC nucleic acid molecules derived from parasitic helminths; as such the proteins and nucleic acid molecules can be isolated from an organism or prepared recombinantly or synthetically. As used herein, the terms Di-ADC proteins and Di-ADC nucleic acid molecules refer to ADC proteins and ADC nucleic acid molecules derived from parasitic helminths of the species *Dirofilaria immitis* and the terms isolated Bm-ADC proteins and isolated Bm-ADC nucleic acid molecules refer to ADC proteins and ADC nucleic acid molecules derived from parasitic helminths of the species *Brugia malayi*. *Dirofilaria immitis* nucleic acid molecules of known length are denoted "nDiADC$_{\#}$" (for example nDiADC$_{808}$) wherein "#" refers to the number of nucleotides in that molecule, and *D. immitis* proteins of known length are denoted "PDiADC$_{\#}$" (for example PDiADC$_{269}$) wherein "#" refers to the number of amino acid residues in that molecule. Similarly, *Brugia malayi* nucleic acid molecules and proteins of known length are denoted "nBmADC$_{\#}$" and "PBmADC$_{\#}$", respectively. The proteins and nucleic acid molecules of the present invention can be obtained from their natural source, or can be produced using, for example, recombinant nucleic acid technology or chemical synthesis. Also included in the present invention is the use of these proteins, nucleic acid molecules, antibodies, and inhibitory compounds as therapeutic compositions to protect animals from parasitic helminth diseases as well as in other applications, such as those disclosed below.

Parasitic helminth ADC proteins and nucleic acid molecules of the present invention have utility because they represent novel targets for anti-parasite vaccines and chemotherapeutic drugs. The products and processes of the present invention are advantageous because they enable the inhibition of crucial steps in parasitic helminth development that involve parasitic helminth ADC. While not being bound by theory, it is believed that parasitic helminth ADC activity is essential for successful migration and development of parasitic helminth larvae.

As described in more detail in the Examples, it was very difficult to initially purify a native ADC protein from *D. immitis* and to isolate a *D. immitis* ADC nucleic acid molecule. For example, Richer et al., ibid., taught that *D. immitis* L3/L4 ES and extract contained metalloaminopeptidase activity based on substrate cleavage and activity inhibition data. The present invention, in contrast, surprisingly showed that at least a portion of the enzyme activity reported in *D. immitis* L3/L4 ES is due to an aromatic amino acid decarboxylase. The present invention further demonstrates the ability to purify ADC from *D. immitis* by following its ADC activity. The present invention also includes the successful, albeit difficult, cloning of cDNA molecules encoding ADC proteins of the present invention in spite of the low homology between *C. elegans* putative ADC-like nucleic acid sequences (EMBL accession No. Z49068) and Di-ADC nucleic acid molecules of the present invention.

One embodiment of the present invention is an isolated protein that includes a parasitic helminth ADC protein. It is to be noted that the term "a" or "an" entity refers to one or more of that entity; for example, a protein, a nucleic acid molecule, an antibody, an inhibitor, a compound or a therapeutic composition refers to "one or more" or "at least one" protein, nucleic acid molecule, antibody, inhibitor, compound or therapeutic composition respectively. As such, the terms "a" (or "an"), "one or more" and "at least one" can be used interchangeably herein. It is also to be noted that the terms "comprising", "including", and "having" can be used interchangeably. According to the present invention, an isolated, or biologically pure, protein, is a protein that has been removed from its natural milieu. As such, "isolated" and "biologically pure" do not necessarily reflect the extent to which the protein has been purified. An isolated protein of the present invention can be obtained from its natural source, can be produced using recombinant DNA technology, or can be produced by chemical synthesis.

As used herein, an isolated parasitic helminth ADC protein of the present invention can be a full-length protein or any homologue of such a protein. An isolated protein of the present invention, including a homologue, can be identified in a straight-forward manner by the protein's ability to elicit an immune response against a parasitic helminth ADC protein or by the protein's ADC activity. Examples of parasitic helminth ADC homologue proteins include parasitic helminth ADC proteins in which amino acids have been deleted (e.g., a truncated version of the protein, such as a peptide), inserted, inverted, substituted and/or derivatized (e.g., by glycosylation, phosphorylation, acetylation, myristoylation, prenylation, palmitoylation, amidation and/or addition of glycerophosphatidyl inositol) such that the homologue includes at least one epitope capable of eliciting an immune response against a parasitic helminth ADC protein, and/or of binding to an antibody directed against a parasitic helminth ADC protein. That is, when the homologue is administered to an animal as an immunogen, using techniques known to those skilled in the art, the animal will produce an immune response against at least one epitope of a natural parasitic helminth ADC protein. The ability of a protein to effect an immune response can be measured using techniques known to those skilled in the art. As used herein, the term "epitope" refers to the smallest portion of a protein or other antigen capable of selectively binding to the antigen binding site of an antibody or a T-cell receptor. It is well accepted by those skilled in the art that the minimal size of a protein epitope is about four to six amino acids. As is appreciated by those skilled in the art, an epitope can include amino acids that naturally are contiguous to each other as well as amino acids that, due to the tertiary structure of the natural protein, are in sufficiently close proximity to form an epitope. According to the present invention, an epitope includes a portion of a protein comprising at least about 4 amino acids, at least about 5 amino acids, at least about 6 amino acids, at least about 10 amino acids, at least about 15 amino acids, at least about 20 amino acids, at least about 25 amino acids, at least about 30 amino acids, at least about 35 amino acids, at least about 40 amino acids or at least about 50 amino acids. In one embodiment of the present invention a parasitic helminth homologue protein has ADC activity. Examples of methods to detect ADC activity are disclosed herein.

Parasitic helminth ADC homologue proteins can be the result of natural allelic variation or natural mutation. Parasitic helminth ADC protein homologues of the present invention can also be produced using techniques known in the art including, but not limited to, direct modifications to the protein or modifications to the gene encoding the protein using, for example, classic or recombinant DNA techniques to effect random or targeted mutagenesis.

Parasitic helminth ADC proteins of the present invention are encoded by parasitic helminth ADC nucleic acid molecules. As used herein, a parasitic helminth ADC nucleic acid molecule includes nucleic acid sequences related to a natural parasitic helminth ADC gene, and, preferably, to either a Dirofilaria ADC gene or a Brugia ADC gene, and more preferably to either a *Dirofilaria immitis* ADC gene or a *Brugia malayi* ADC gene. Other examples of parasitic helminths from which to isolate proteins, genes and nucleic acid molecules are disclosed herein. As used herein, a parasitic helminth ADC gene includes all regions such as regulatory regions that control production of the parasitic helminth ADC protein encoded by the gene (such as, but not limited to, transcription, translation or post-translation control regions) as well as the coding region itself, and any introns or non-translated coding regions. As used herein, a gene that "includes" or "comprises" a sequence may include that sequence in one contiguous array, or may include the sequence as fragmented exons. As used herein, the term "coding region" refers to a continuous linear array of nucleotides that translates into a protein. A full-length coding region is that coding region that is translated into a full-length, i.e., a complete protein as would be initially translated in its natural millieu, prior to any post-translational modifications.

One embodiment of the present invention is a *D. immitis* ADC gene that includes the nucleic acid sequence SEQ ID NO:5, SEQ ID NO:9, SEQ ID NO:13, and/or SEQ ID NO:16, as well as the complements of any of these nucleic acid sequences. These nucleic acid sequences are further described herein. For example, nucleic acid sequence SEQ ID NO:16 represents the deduced sequence of the coding strand of a cDNA (complementary DNA) denoted herein as *D. immitis* ADC nucleic acid molecule nDiADC$_{808}$, the production of which is disclosed in the Examples. Nucleic acid molecule nDiADC$_{808}$ comprises an apparently non-full-length coding region. The complement of SEQ ID NO:16 (represented herein by SEQ ID NO:18) refers to the nucleic acid sequence of the strand complementary to the strand having SEQ ID NO:16, which can easily be determined by those skilled in the art. Likewise, a nucleic acid sequence complement of any nucleic acid sequence of the present invention refers to the nucleic acid sequence of the nucleic acid strand that is complementary to (i.e., can form a double helix with) the strand for which the sequence is cited. It should be noted that since nucleic acid sequencing technology is not entirely error-free, SEQ ID NO:16 (as well as other nucleic acid and protein sequences presented herein) represents an apparent nucleic acid sequence of the nucleic acid molecule encoding a Di-ADC protein of the present invention.

Another embodiment of the present invention is a *B. malayi* ADC gene that includes the nucleic acid sequence SEQ ID NO:20, as well as the complement of SEQ ID NO:22. Nucleic acid sequence SEQ ID NO:20 represents the deduced sequence of the coding strand of a cDNA (complementary DNA) denoted herein as *B. malayi* ADC nucleic acid molecule nBmADC$_{549}$, the production of which is disclosed in the Examples. Nucleic acid molecule nBmADC$_{549}$ comprises an apparently non-full-length coding region. The complement of SEQ ID NO:20 (represented herein by SEQ ID NO:22) refers to the nucleic acid sequence of the strand complementary to the strand having SEQ ID NO:20, which can easily be determined by those skilled in the art.

In another embodiment, a Di-ADC gene or nucleic acid molecule can be an allelic variant that includes a similar but not identical sequence to SEQ ID NO:16, SEQ ID NO:18, or any other *D. immitis* nucleic acid sequence cited herein. Furthermore, a Bm-ADC gene or nucleic acid molecule can be an allelic variant that includes a similar but not identical sequence to SEQ ID NO:19 or SEQ ID NO:21. For example, an allelic variant of a Di-ADC gene including SEQ ID NO:16 and SEQ ID NO:18, is a gene that occurs at essentially the same locus (or loci) in the genome as the gene including SEQ ID NO:16 and SEQ ID NO:18, but which, due to natural variations caused by, for example, mutation or recombination, has a similar but not identical sequence. Because natural selection typically selects against alterations that affect function, allelic variants (i.e. alleles corresponding to, or of, cited nucleic acid sequences) usually encode proteins having similar activity to that of the protein encoded by the gene to which they are being compared. Allelic variants of genes or nucleic acid molecules can also comprise alterations in the 5' or 3' untranslated regions of the gene (e.g., in regulatory control regions), or can involve alternative splicing of a nascent transcript, thereby bringing alternative exons into juxtaposition. Allelic variants are well known to those skilled in the art and would be expected to occur naturally within a given parasitic helminth such as Dirofilaria or Brugia, since the respective genomes are diploid, and sexual reproduction will result in the reassortment of alleles.

In one embodiment of the present invention, an isolated ADC protein is encoded by a nucleic acid molecule that hybridizes under stringent hybridization conditions to a gene encoding a parasitic helminth ADC protein. The minimal size of an ADC protein of the present invention is a size sufficient to be encoded by a nucleic acid molecule capable of forming a stable hybrid (i.e., hybridizing under stringent hybridization conditions) with the complementary sequence of a nucleic acid molecule encoding the corresponding natural protein. The size of a nucleic acid molecule encoding such a protein is dependent on the nucleic acid composition and the percent homology between the parasitic helminth ADC nucleic acid molecule and the complementary nucleic acid sequence. It can easily be understood that the extent of homology required to form a stable hybrid under stringent conditions can vary depending on whether the homologous sequences are interspersed throughout a given nucleic acid molecule or are clustered (i.e., localized) in distinct regions on a given nucleic acid molecule.

The minimal size of a nucleic acid molecule capable of forming a stable hybrid with a gene encoding a parasitic helminth ADC protein is typically at least about 12 to about 15 nucleotides in length if the nucleic acid molecule is GC-rich and at least about 15 to about 17 bases in length if it is AT-rich. The minimal size of a nucleic acid molecule used to encode an ADC protein homologue of the present invention is from about 12 to about 18 nucleotides in length. Thus, the minimal size of an ADC protein homologue of the present invention is from about 4 to about 6 amino acids in length. There is no limit, other than a practical limit, on the maximal size of a nucleic acid molecule encoding a parasitic helminth ADC protein of the present invention because a nucleic acid molecule of the present invention can include a portion of a gene, an entire gene, or multiple genes. The preferred size of a protein encoded by a nucleic acid molecule of the present invention depends on whether a full-length, fusion, multivalent, or functional portion of such a protein is desired.

Stringent hybridization conditions are determined based on defined physical properties of the gene to which the nucleic acid molecule is being hybridized, and can be defined mathematically. Stringent hybridization conditions are those experimental parameters that allow an individual skilled in the art to identify significant similarities between heterologous nucleic acid molecules. These conditions are well known to those skilled in the art. See, for example, Sambrook, et al., 1989, *Molecular Cloning: A Laboratory Manual*, Cold Spring Harbor Labs Press, and Meinkoth, et al., 1984, *Anal. Biochem.* 138, 267–284. As explained in detail in the cited references, the determination of hybridization conditions involves the manipulation of a set of variables including the ionic strength (M, in moles/liter), the hybridization temperature (° C.), the concentration of nucleic acid helix destabilizing agents (such as formamide), the average length of the shortest hybrid duplex (n), and the percent G+C composition of the fragment to which an unknown nucleic acid molecule is being hybridized. For nucleic acid molecules of at least about 150 nucleotides, these variables are inserted into a standard mathematical formula to calculate the melting temperature, or $T_m$, of a given nucleic acid molecule. As defined in the formula below, $T_m$ is the temperature at which two complementary nucleic acid molecule strands will disassociate, assuming 100% complementarity between the two strands:

$$T_m = 81.5° C. + 16.6 \log M + 0.41(\% \; G+C) - 500/n - 0.61(\% \text{ formamide}).$$

For nucleic acid molecules smaller than about 50 nucleotides, hybrid stability is defined by the dissociation temperature ($T_d$), which is defined as the temperature at which 50% of the duplexes dissociate. For these smaller molecules, the stability at a standard ionic strength is defined by the following equation:

$$T_d = 4(G+C) + 2(A+T).$$

A temperature of 5° C. below $T_d$ is used to detect hybridization between perfectly matched molecules.

Also well known to those skilled in the art is how base-pair mismatch, i.e. differences between two nucleic acid molecules being compared, including non-complementarity of bases at a given location, and gaps due to insertion or deletion of one or more bases at a given location on either of the nucleic acid molecules being compared, will affect $T_m$ or $T_d$ for nucleic acid molecules of different sizes. For example, $T_m$ decreases about 1° C. for each 1% of mismatched base-pairs for hybrids greater than about 150 bp, and $T_d$ decreases about 5° C. for each mismatched base-pair for hybrids below about 50 bp. Conditions for hybrids between about 50 and about 150 base-pairs can be determined empirically and without undue experimentation using standard laboratory procedures well known to those skilled in the art. These simple procedures allow one skilled in the art to set the hybridization conditions (by altering, for example, the salt concentration, the formamide concentration or the temperature) so that only nucleic acid hybrids with less than a specified % base-pair mismatch will hybridize. Stringent hybridization conditions are commonly understood by those skilled in the art to be those experimental conditions that will allow hybridization between molecules having about 30% or less base-pair mismatch (i.e., about 70% or greater identity). Because one skilled in the art can easily determine whether a given nucleic acid molecule to be tested is less than or greater than about 50 nucleotides, and can therefore choose the appropriate formula for determining hybridization conditions, he or she can determine whether the nucleic acid molecule will hybridize with a given gene under stringent hybridization conditions and similarly whether the nucleic acid molecule will hybridize under conditions designed to allow a desired amount of base pair mismatch.

Hybridization reactions are often carried out by attaching the nucleic acid molecule to be hybridized to a solid support such as a membrane, and then hybridizing with a labeled nucleic acid molecule, typically referred to as a probe, suspended in a hybridization solution. Examples of common hybridization reaction techniques include, but are not limited to, the well-known Southern and northern blotting procedures. Typically, the actual hybridization reaction is done under non-stringent conditions, i.e., at a lower temperature and/or a higher salt concentration, and then high stringency is achieved by washing the membrane in a solution with a higher temperature and/or lower salt concentration in order to achieve the desired stringency.

For example, if the skilled artisan wished to identify a nucleic acid molecule that hybridizes under stringent hybridization conditions with a *Dirofilaria immitis* nucleic acid molecule of about 150 bp in length, the following conditions could preferably be used. The average G+C content of *D. immitis* DNA is about 35%. The unknown nucleic acid molecules would be attached to a support membrane, and the 150 bp probe would be labeled, e.g. with a radioactive tag. The hybridization reaction could be carried out in a solution comprising 2× SSC and 0% formamide, at a temperature of about 37° C. (low stringency conditions). Solutions of differing concentrations of SSC can be made by one of skill in the art by diluting a stock solution of 20× SSC (175.3 gram NaCl and about 88.2 gram sodium citrate in 1 liter of water, pH 7) to obtain the desired concentration of SSC. In order to achieve high stringency hybridization, the skilled artisan would calculate the washing conditions required to allow up to 30% base-pair mismatch. For example, in a wash solution comprising 1× SSC and 0% formamide, the $T_m$ of perfect hybrids would be about 79° C.:

$$81.5°\,C.+16.6log(0.15M)+(0.41\times35)-(500/150)-(0.61\times0)=79°\,C.$$

Thus, to achieve hybridization with nucleic acid molecules having about 30% base-pair mismatch, hybridization washes would be carried out at a temperature of about 49° C. It is thus within the skill of one in the art to calculate additional hybridization temperatures based on the desired percentage base-pair mismatch, formulae and G/C content disclosed herein. For example, it is appreciated by one skilled in the art that as the nucleic acid molecule to be tested for hybridization against nucleic acid molecules of the present invention having sequences specified herein becomes longer than 150 nucleotides, the $T_m$ for a hybridization reaction allowing up to 30% base-pair mismatch will not vary significantly from 49° C.

Furthermore, it is known in the art that there are commercially available computer programs for determining the degree of similarity between two nucleic acid sequences. These computer programs include various known methods to determine the percentage identity and the number and length of gaps between hybrid nucleic acid molecules. Preferred methods to determine the percent identity among amino acid sequences and also among nucleic acid sequences include analysis using one or more of the commercially available computer programs designed to compare and analyze nucleic acid or amino acid sequences. These computer programs include, but are not limited to, GCG™ (available from Genetics Computer Group, Madison, Wis.), DNAsis™ (available from Hitachi Software, San Bruno, Calif.) and MacVector™ (available from the Eastman Kodak Company, New Haven, Conn.). A preferred method to determine percent identity among amino acid sequences and also among nucleic acid sequences includes using the Compare function by maximum matching within the program DNAsis Version 2.1 using default parameters.

One embodiment of the present invention includes parasitic helminth ADC proteins. A preferred parasitic helminth ADC protein includes a protein encoded by a nucleic acid molecule which is at least about 50 nucleotides and which hybridizes under conditions which preferably allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:7, SEQ ID NO:11, SEQ ID NO:15, SEQ ID NO:18 and SEQ ID NO:21.

Another preferred parasitic helminth ADC protein of the present invention includes a protein encoded by a nucleic acid molecule which is at least about 150 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:7, SEQ ID NO:11, SEQ ID NO:15, SEQ ID NO:18 and SEQ ID NO:21.

Another embodiment of the present invention includes a parasitic helminth ADC protein encoded by a nucleic acid molecule comprising at least about 150 base-pairs, wherein said nucleic acid molecule hybridizes, in a solution comprising 1× SSC and 0% formamide, at a temperature of about 49° C., to an isolated nucleic acid molecule selected from the group consisting of SEQ ID NO:7, SEQ ID NO:11, SEQ ID NO:15, SEQ ID NO:18 and SEQ ID NO:21. Additional preferred parasitic helminth ADC proteins include proteins encoded by oligonucleotides of an isolated nucleic acid molecule comprising at least about 150 base-pairs, wherein said nucleic acid molecule hybridizes, in a solution comprising 1× SSC and 0% formamide, at a temperature of about 49° C., to an isolated nucleic acid molecule selected from the group consisting of SEQ ID NO:7, SEQ ID NO:11, SEQ ID NO:15, SEQ ID NO:18 and SEQ ID NO:21, wherein said oligonucleotide comprises at least about 50 nucleotides.

Another preferred parasitic helminth ADC protein of the present invention includes a protein which is encoded by a nucleic acid molecule that is preferably about 80% identical, more preferably about 85% identical, more preferably about 90% identical, and even more preferably about 95% identical to a nucleic acid molecule having the nucleic acid sequence SEQ ID NO:5, SEQ ID NO:9, SEQ ID NO:13, SEQ ID NO:16, or SEQ ID NO:19; also preferred are fragments (i.e. portions) of such proteins encoded by nucleic acid molecules which are at least about 50 nucleotides.

Yet another preferred parasitic helminth ADC protein of the present invention includes a protein encoded by a nucleic acid molecule which is preferably about 70% identical, more preferably about 75% identical, more preferably about 80% identical, more preferably about 85% identical, more preferably about 90% identical and even more preferably about 95% identical to a nucleic acid molecule having the nucleic acid sequence SEQ ID NO:5, SEQ ID NO:9, SEQ ID NO:13, SEQ ID NO:16, and/or SEQ ID NO:19; also preferred are fragments of such proteins encoded by a nucleic acid molecule which is at least about 150 nucleotides. Percent identity as used herein is determined using the Compare function by maximum matching within the program DNAsis Version 2.1 using default parameters.

Additional preferred parasitic helminth proteins of the present invention include proteins having the amino acid sequence SEQ ID NO:6, SEQ ID NO:10, SEQ ID NO:14, SEQ ID NO:17, or SEQ ID NO:20 and proteins comprising homologues of a protein having the amino acid sequence SEQ ID NO:6, SEQ ID NO:10, SEQ ID NO:14, SEQ ID NO:17, and/or SEQ ID NO:20 wherein such a homologue comprises at least one epitope that elicits an immune response against a protein having an amino acid sequence SEQ ID NO:6, SEQ ID NO:10, SEQ ID NO:14, SEQ ID NO:17, and/or SEQ ID NO:20. Likewise, also preferred are proteins encoded by nucleic acid molecules encoded by nucleic acid molecules having nucleic acid sequence SEQ ID NO:5, SEQ ID NO:9, SEQ ID NO:13, SEQ ID NO:16, and/or SEQ ID NO:19, or by homologues thereof.

A preferred isolated protein of the present invention is a protein encoded by at least one of the following nucleic acid molecules: $nDiADC_{456}$, $nDiADC_{475}$, $nDiADC_{517}$, $nDiADC_{808}$ and $nBmADC_{549}$, or allelic variants of any of these nucleic acid molecules. Another preferred isolated protein is encoded by a nucleic acid molecule having nucleic acid sequence SEQ ID NO:5, SEQ ID NO:9, SEQ ID NO:13, SEQ ID NO:16, and/or SEQ ID NO:19; or a protein encoded by an allelic variant of any of these listed nucleic acid molecule.

Translation of SEQ ID NO:5, the coding strand of $nDiADC_{456}$, yields a protein of about 152 amino acids, denoted herein as $PDiADC_{152}$, the amino acid sequence of which is presented in SEQ ID NO:6, assuming a first in-frame codon extending from nucleotide 1 to nucleotide 3 of SEQ ID NO:5.

Translation of SEQ ID NO:9, the coding strand of $nDiADC_{457}$, yields a protein of about 158 amino acids, denoted herein as PDiADC$_{158}$, the amino acid sequence of which is presented in SEQ ID NO:10, assuming a first in-frame codon extending from nucleotide 1 to nucleotide 3 of SEQ ID NO:9.

Translation of SEQ ID NO:13, the coding strand of nDiADC$_{517}$, yields a protein of about 172 amino acids, denoted herein as PDiADC$_{172}$, the amino acid sequence of which is presented in SEQ ID NO:14, assuming a first in-frame codon extending from nucleotide 1 to nucleotide 3 of SEQ ID NO:13.

Translation of SEQ ID NO:16, the coding strand of nDiADC$_{808}$, yields a protein of about 269 amino acids, denoted herein as PDiADC$_{269}$, the amino acid sequence of which is presented in SEQ ID NO:17, assuming a first in-frame codon extending from nucleotide 1 to nucleotide 3 of SEQ ID NO:16.

Translation of SEQ ID NO:19, the coding strand of nBmADC$_{549}$, yields a protein of about 183 amino acids, denoted herein as PBmADC$_{183}$, the amino acid sequence of which is presented in SEQ ID NO:20, assuming a first in-frame codon extending from nucleotide 1 to nucleotide 3 of SEQ ID NO:19.

Preferred ADC proteins of the present invention include proteins that are at least about 90%, preferably at least about 92%, more preferably at least about 95%, even more preferably at least about 98%, and even more preferably about 100% identical to PDiADC$_{269}$. More preferred are ADC proteins comprising PDiADC$_{152}$, PDiADC$_{158}$, PDiADC$_{172}$, PDiADC$_{269}$, or PBmADC$_{183}$; and proteins encoded by allelic variants of a nucleic acid molecules encoding proteins PDiADC$_{152}$, PDiADC$_{158}$, PDiADC$_{172}$, PDiADC$_{269}$, or PBmADC$_{183}$. Also preferred are fragments thereof having at least about 35 amino acid residues.

Other preferred ADC proteins of the present invention include proteins having amino acid sequences that are at least about 90%, preferably at least about 92%, more preferably at least about 95%, even more preferably at least about 98%, and even more preferably about 100% identical to amino acid sequence SEQ ID NO:6, SEQ ID NO:10, SEQ ID NO:14, SEQ ID NO:17, and/or SEQ ID NO:20. More preferred are ADC proteins comprising amino acid sequences SEQ ID NO:6, SEQ ID NO:10, SEQ ID NO:14, SEQ ID NO:17, and/or SEQ ID NO:20; and ADC proteins encoded by allelic variants of nucleic acid molecules encoding ADC proteins having amino acid sequences SEQ ID NO:6, SEQ ID NO:10, SEQ ID NO:14, SEQ ID NO:17, and/or SEQ ID NO:20. Also preferred are fragments thereof having at least about 35 amino acid residues.

In one embodiment of the present invention, Dirofilaria ADC proteins comprise amino acid sequence SEQ ID NO:17 (including, but not limited to, the proteins consisting of amino acid sequence SEQ ID NO:17, fusion proteins and multivalent proteins), and proteins encoded by allelic variants of nucleic acid molecules encoding proteins having amino acid sequence SEQ ID NO:17. In another embodiment, Brugia ADC proteins of the present invention comprise amino acid sequence SEQ ID NO:20 (including, but not limited to, the proteins consisting of amino acid sequence SEQ ID NO:20, fusion proteins and multivalent proteins), and proteins encoded by allelic variants of nucleic acid molecules encoding proteins having amino acid sequence SEQ ID NO:20.

In one embodiment, a preferred Di-ADC protein comprises an amino acid sequence of at least about 35 amino acids in length, preferably at least about 50 amino acids in length, more preferably at least about 100 amino acids in length, more preferably at least about 200 amino acids in length, even more preferably at least about 250 amino acids in length and a preferred Bm-ADC protein comprises an amino acid sequence of at least about 35 amino acids in length, preferably at least about 50 amino acids in length, more preferably at least about 100 amino acids in length, more preferably at least about 150 amino acids in length, even more preferably at least about 180 amino acids in length. Within this embodiment, a preferred D. immitis ADC protein of the present invention has an amino acid sequence comprising at least a portion of SEQ ID NO:17 and a B. malayi ADC protein has an amino acid sequence comprising at least a portion of SEQ ID NO:20. In another embodiment, a preferred parasitic helminth ADC protein comprises a full-length protein, i.e., a protein encoded by a full-length coding region.

Additional preferred ADC proteins of the present invention include proteins encoded by nucleic acid molecules comprising at least a portion of nDiADC$_{456}$, nDiADC$_{475}$, nDiADC$_{517}$, nDiADC$_{808}$ and nBmADC$_{549}$, as well as ADC proteins encoded by allelic variants of such nucleic acid molecules.

Also preferred are ADC proteins encoded by nucleic acid molecules having nucleic acid sequences comprising at least a portion of SEQ ID NO:5, SEQ ID NO:9, SEQ ID NO:13, SEQ ID NO:16 and/or SEQ ID NO:19, as well as allelic variants of these nucleic acid molecules.

In another embodiment, a preferred D. immitis ADC protein of the present invention is encoded by a nucleic acid molecule comprising at least about 50 nucleotides, preferably at least about 100 nucleotides, more preferably at least about 350 nucleotides, more preferably at least about 450 nucleotides, more preferably at least about 500 nucleotides, and even more preferably at least about 800 nucleotides, and a preferred B. malayi protein of the present invention is encoded by nucleic acid molecule comprises a coding region of at least about 50 nucleotides, preferably at least about 100 nucleotides, more preferably at least about 350 nucleotides, more preferably at least about 500 nucleotides even more preferably at least about 550 nucleotides. Within this embodiment is an ADC protein encoded by at least a portion nDiADC$_{808}$ or by an allelic variant of this nucleic acid molecule or nBmADC$_{549}$ or by an allelic variant of this nucleic acid molecule. In yet another embodiment, a preferred parasitic helminth ADC protein of the present invention is encoded by a nucleic acid molecule comprising an apparently full-length ADC coding region, i.e., a nucleic acid molecule encoding an apparently full-length ADC protein.

A preferred parasitic helminth ADC protein of the present invention is a compound that when administered to an animal in an effective manner, is capable of protecting that animal from disease caused by a parasitic helminth. In accordance with the present invention, the ability of an ADC protein of the present invention to protect an animal from disease by a parasitic helminth refers to the ability of that protein to, for example, treat, ameliorate and/or prevent disease caused by parasitic helminths. In one embodiment, a parasitic helminth ADC protein of the present invention can elicit an immune response (including a humoral and/or cellular immune response) against a parasitic helminth.

Suitable parasitic helminths to target include any parasitic helminth that is essentially incapable of causing disease in an animal administered a parasitic helminth ADC protein of the present invention. As such, parasitic helminths to target includes any parasitic helminth that produces a protein having one or more epitopes that can be targeted by a humoral and/or cellular immune response against a parasitic helminth ADC protein of the present invention and/or that can be targeted by an inhibitory compound that otherwise inhibits parasitic helminth ADC function (e.g., a compound that binds to parasitic helminth ADC thereby blocking parasitic helminth development and/or migration regulatory pathways), thereby resulting in the decreased ability of the parasite to cause disease in an animal. Preferred parasitic helminths to target include nematodes, cestodes, and trematodes, with nematodes being preferred. Preferred parasitic helminths to target include filariid, ascarid, capillarid, strongylid, strongyloides, trichostrongyle, and trichurid nematodes. Particularly preferred nematodes are those of the genera Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris. Uncinaria. and Wuchereria. Preferred filariid nematodes include Dirofilaria, Onchocerca, Acanthocheilonema, Brugia, Dipetalonema, Loa, Parafilaria, Setaria, Stephanofilaria and Wuchereria filariid nematodes, with *Dirofilaria immitis, Onchocerca volvulus* and *Brugia malayi* being even more preferred.

One embodiment of a parasitic helminth ADC protein of the present invention is a fusion protein that includes a parasitic helminth ADC protein-containing domain attached to one or more fusion segments. Suitable fusion segments for use with the present invention include, but are not limited to, segments that can: enhance a protein's stability; act as an immunopotentiator to enhance an immune response against a parasitic helminth ADC protein; and/or assist in purification of a parasitic helminth ADC protein (e.g., by affinity chromatography). A suitable fusion segment can be a domain of any size that has the desired function (e.g., imparts increased stability, imparts increased immunogenicity to a protein, and/or simplifies purification of a protein). Fusion segments can be joined to amino and/or carboxyl termini of the parasitic helminth ADC-containing domain of the protein and can be susceptible to cleavage in order to enable straight-forward recovery of a parasitic helminth ADC protein. Fusion proteins are preferably produced by culturing a recombinant cell transformed with a fusion nucleic acid molecule that encodes a protein including the fusion segment attached to either the carboxyl and/or amino terminal end of an ADC-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, a T7 tag peptide, a Flag™ peptide, or other domains that can be purified using compounds that bind to the domain, such as monoclonal antibodies). More preferred fusion segments include metal binding domains, such as a poly-histidine segment; a maltose binding domain; a strep tag peptide, such as that available from Biometra in Tampa, Fla.; and an S10 peptide.

In another embodiment, a parasitic helminth ADC protein of the present invention also includes at least one additional protein segment that is capable of protecting an animal from one or more diseases. Such a multivalent protective protein can be produced by culturing a cell transformed with a nucleic acid molecule comprising two or more nucleic acid domains joined together in such a manner that the resulting nucleic acid molecule is expressed as a multivalent protective compound containing at least two protective compounds capable of protecting an animal from diseases caused, for example, by at least one infectious agent.

Examples of multivalent protective compounds include, but are not limited to, a parasitic helminth ADC protein of the present invention attached to one or more compounds protective against one or more other infectious agents, particularly an agent that infects humans, cats, dogs, cattle and/or horses, such as, but not limited to: viruses (e.g., adenoviruses, caliciviruses, coronaviruses, distemper viruses, hepatitis viruses, herpesviruses, immunodeficiency viruses, infectious peritonitis viruses, leukemia viruses, oncogenic viruses, panleukopenia viruses, papilloma viruses, parainfluenza viruses, parvoviruses, rabies viruses, and reoviruses, as well as other cancer-causing or cancer-related viruses); bacteria (e.g., Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia; fungi and fungal-related microorganisms (e.g., Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha; and other parasites (e.g., Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, as well as helminth parasites, such as those disclosed herein). In one embodiment, a parasitic helminth ADC protein of the present invention is attached to one or more additional compounds protective against diseases caused by parasitic helminths, for example heartworm disease or elephantiasis. In another embodiment, one or more protective compounds, such as those listed above, can be included in a multivalent vaccine comprising a parasitic helminth ADC protein of the present invention and one or more other protective molecules as separate compounds.

The present invention also includes mimetopes of parasitic helminth ADC proteins of the present invention. As used herein, a mimetope of a parasitic helminth ADC protein of the present invention refers to any compound that is able to mimic the activity of such an ADC protein, often because the mimetope has a structure that mimics the particular ADC protein. Mimetopes can be, but are not limited to: peptides that have been modified to decrease their susceptibility to degradation such as all-D retro peptides; anti-idiotypic and/ or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of proteins of the present invention. Mimetopes can also be obtained by generating random samples of molecules, such as oligonucleotides, peptides or other organic molecules, and screening such samples by affinity chromatography techniques using the corresponding binding partner.

Another embodiment of the present invention is an isolated nucleic acid molecule comprising a parasitic helminth ADC nucleic acid molecule. The identifying characteristics of such nucleic acid molecules are heretofore described. A nucleic acid molecule of the present invention can include an isolated natural parasitic helminth ADC gene or a homologue thereof, the latter of which is described in more detail below. A nucleic acid molecule of the present invention can include one or more regulatory regions, full-length or partial coding regions, or combinations thereof. The minimal size of a nucleic acid molecule of the present invention is a size sufficient to allow the formation of a stable hybrid (i.e., hybridization under stringent hybridization conditions) with the complementary sequence of another nucleic acid molecule. As such, the minimal size of an ADC nucleic acid molecule of the present invention is from about 12 to about 18 nucleotides in length. Suitable and preferred parasitic helminths from which to isolate nucleic acid molecules of the present invention are disclosed herein. Particularly preferred ADC nucleic acid molecules include *D. immitis* and *B. malayi* ADC nucleic acid molecules.

In accordance with the present invention, an isolated nucleic acid molecule is a nucleic acid molecule that has been removed from its natural milieu (i.e., that has been subjected to human manipulation) and can include DNA, RNA, or derivatives of either DNA or RNA. As such, "isolated" does not reflect the extent to which the nucleic acid molecule has been purified. An isolated parasitic helminth ADC nucleic acid molecule of the present invention, or a homologue thereof, can be isolated from its natural source or produced using recombinant DNA technology (e.g., polymerase chain reaction (PCR) amplification or cloning) or chemical synthesis. Isolated parasitic helminth ADC nucleic acid molecules, and homologues thereof, can include, for example, natural allelic variants and nucleic acid molecules modified by nucleotide insertions, deletions, substitutions, and/or inversions in a manner such that the modifications do not substantially interfere with the nucleic acid molecule's ability to encode an ADC protein of the present invention.

A parasitic helminth ADC nucleic acid molecule homologue can be produced using a number of methods known to those skilled in the art, see, for example, Sambrook et al., 1989, *Molecular Cloning: A Laboratory Manual*, Cold Spring Harbor Labs Press. For example, nucleic acid molecules can be modified using a variety of techniques including, but not limited to, classic mutagenesis and recombinant DNA techniques such as site-directed mutagenesis, chemical treatment, restriction enzyme cleavage, ligation of nucleic acid fragments, PCR amplification, synthesis of oligonucleotide mixtures and ligation of mixture groups to "build" a mixture of nucleic acid molecules, and combinations thereof. Nucleic acid molecule homologues can be selected by hybridization with a parasitic helminth ADC nucleic acid molecule or by screening the function of a protein encoded by the nucleic acid molecule (e.g., ability to elicit an immune response against at least one epitope of a parasitic helminth ADC protein or to effect ADC activity).

An isolated nucleic acid molecule of the present invention can include a nucleic acid sequence that encodes at least one parasitic helminth ADC protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a parasitic helminth ADC protein.

A preferred nucleic acid molecule of the present invention, when administered to an animal, is capable of protecting that animal from disease caused by a parasitic helminth. As will be disclosed in more detail below, such a nucleic acid molecule can be, or encode, an antisense RNA, a molecule capable of triple helix formation, a ribozyme, or other nucleic acid-based drug compound. In additional embodiments, a nucleic acid molecule of the present invention can encode a protective protein (e.g., an ADC protein of the present invention), the nucleic acid molecule being delivered to the animal, for example, by direct injection (i.e, as a genetic vaccine) or in a vehicle such as a recombinant virus vaccine or a recombinant cell vaccine.

In one embodiment of the present invention, a preferred parasitic helminth ADC nucleic acid molecule includes an isolated nucleic acid molecule which is at least about 50 nucleotides and which hybridizes under conditions which preferably allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:5, SEQ ID NO:7, SEQ ID NO:9, SEQ ID NO:11, SEQ ID NO:13, SEQ ID NO:15, SEQ ID NO:16, SEQ ID NO:18, SEQ ID NO:19 and SEQ ID NO:21.

Another preferred parasitic helminth ADC nucleic acid molecule of the present invention includes a nucleic acid molecule which is at least about 150 nucleotides and which hybridizes under conditions which preferably allow about 30% base pair mismatch, more preferably under conditions which allow about 25% base pair mismatch, more preferably under conditions which allow about 20% base pair mismatch, more preferably under conditions which allow about 15% base pair mismatch, more preferably under conditions which allow about 10% base pair mismatch and even more preferably under conditions which allow about 5% base pair mismatch with a nucleic acid molecule selected from the group consisting of SEQ ID NO:5, SEQ ID NO:7, SEQ ID NO:9, SEQ ID NO:1, SEQ ID NO:13, SEQ ID NO:15, SEQ ID NO:16, SEQ ID NO:18, SEQ ID NO:19 and SEQ ID NO:21.

Another embodiment of the present invention includes a nucleic acid molecule comprising at least about 150 base-pairs, wherein said nucleic acid molecule hybridizes, in a solution comprising 1× SSC and 0% formamide, at a temperature of about 49° C., to an isolated nucleic acid molecule selected from the group consisting of SEQ ID NO:5, SEQ ID NO:7, SEQ ID NO:9, SEQ ID NO:11, SEQ ID NO:13, SEQ ID NO:15, SEQ ID NO:16, SEQ ID NO:18, SEQ ID NO:19 and SEQ ID NO:21. Additional preferred nucleic acid molecules of the present invention include oligonucleotides of an isolated nucleic acid molecule comprising at least about 150 base-pairs, wherein said nucleic acid molecule hybridizes, in a solution comprising 1× SSC and 0% formamide, at a temperature of about 49° C., to an isolated nucleic acid molecule selected from the group consisting of SEQ ID NO:5, SEQ ID NO:7, SEQ ID NO:9, SEQ ID NO:11, SEQ ID NO:13, SEQ ID NO:15, SEQ ID NO:16, SEQ ID NO:18, SEQ ID NO:19 and SEQ ID NO:21, wherein said oligonucleotide comprises at least about 50 nucleotides.

Additional preferred parasitic helminth ADC nucleic acid molecules of the present invention include nucleic acid molecules is at least about 50 nucleotides comprising a nucleic acid sequence that is preferably at least about 80%, more preferably at least about 85%, more preferably at least about 90%, and even more preferably at least about 95% identical to a nucleic acid sequence selected from the group consisting of SEQ ID NO:5, SEQ ID NO:7, SEQ ID NO:9, SEQ ID NO:11, SEQ ID NO:13, SEQ ID NO:15, SEQ ID NO:16, SEQ ID NO:18, SEQ ID NO:19 and SEQ ID NO:21 and nucleic acid molecules is at least about 150 nucleotides comprising a nucleic acid sequence that is preferably at least about 70%, more preferably at least about 75%, more preferably at least about 80%, more preferably at least about 85%, more preferably at least about 90%, and even more preferably at least about 95% identical to a nucleic acid sequence selected from the group consisting of SEQ ID NO:5, SEQ ID NO:7, SEQ ID NO:9, SEQ ID NO:11, SEQ ID NO:13, SEQ ID NO:15, SEQ ID NO:16, SEQ ID NO:18, SEQ ID NO:19 and SEQ ID NO:21. Also preferred are oligonucleotides of any of such nucleic acid molecules, particularly those that are at least about 50 nucleotides. Percent identity may be determined using the Compare function by maximum matching within the program DNAsis Version 2.1 using default parameters.

One embodiment of the present invention is a nucleic acid molecule comprising all or part of nucleic acid molecules nDiADC$_{456}$, nDiADC$_{475}$, nDiADC$_{517}$, nDiADC$_{808}$ and nBmADC$_{549}$, or allelic variants of these nucleic acid molecules. Another preferred nucleic acid molecule of the present invention includes at least a portion of nucleic acid sequence SEQ ID NO:5, SEQ ID NO:7, SEQ ID NO:9, SEQ ID NO:11, SEQ ID NO:13, SEQ ID NO:15, SEQ ID NO:16, SEQ ID NO:18, SEQ ID NO:19 and/or SEQ ID NO:21, as well as allelic variants of nucleic acid molecules having these nucleic acid sequences and homologues of nucleic acid molecules having these nucleic acid sequences; preferably such a homologue encodes or is complementary to a nucleic acid molecule that encodes at least one epitope that elicits and an immune response against a protein having an amino acid sequence SEQ ID NO:6, SEQ ID NO:10, SEQ ID NO:14, SEQ ID NO:17, and/or SEQ ID NO:20. Such nucleic acid molecules can include nucleotides in addition to those included in the SEQ ID NOs, such as, but not limited to, a full-length gene, a full-length coding region, a nucleic acid molecule encoding a fusion protein, or a nucleic acid molecule encoding a multivalent protective compound.

In one embodiment, an ADC nucleic acid molecule of the present invention encodes a protein that is at least about 90%, preferably at least about 92%, more preferably at least about 95%, even more preferably at least about 98%, and even more preferably at least about 100% identical to PDiADC$_{269}$. Even more preferred is a nucleic acid molecule encoding PDiADC$_{152}$, PDiADC$_{158}$, PDiADC$_{172}$, PDiADC$_{269}$, and/or PBmADC$_{183}$, and/or an allelic variant of such a nucleic acid molecule.

In another embodiment, an ADC nucleic acid molecule of the present invention encodes a protein having an amino acid sequence that is at least about 90%, preferably at least about 92%, more preferably at least about 95%, even more preferably at least about 98%, and even more preferably at least about 100% identical to SEQ ID NO:17 or SEQ ID NO:20. The present invention also includes an ADC nucleic acid molecule encoding a protein having at least a portion of SEQ ID NO:6, SEQ ID NO:10, SEQ ID NO:14, SEQ ID NO:17, and/or SEQ ID NO:20, as well as allelic variants of an ADC nucleic acid molecule encoding a protein having these sequences, including nucleic acid molecules that have been modified to accommodate codon usage properties of the cells in which such nucleic acid molecules are to be expressed.

In another embodiment, a preferred parasitic helminth ADC nucleic acid molecule encodes an ADC protein comprising at least about at least about 35 amino acids in length, preferably at least about 50 amino acids in length, more preferably at least about 100 amino acids in length, more preferably at least about 200 amino acids in length, even more preferably at least about 250 amino acids in length.

In yet another embodiment, a preferred parasitic helminth ADC nucleic acid molecule of the present invention comprises an apparently full-length ADC coding region, i.e., the preferred nucleic acid molecule encodes an apparently full-length ADC protein.

Knowing the nucleic acid sequences of certain parasitic helminth ADC nucleic acid molecules of the present invention allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain other parasitic helminth ADC nucleic acid molecules. Such nucleic acid molecules can be obtained in a variety of ways including screening appropriate expression libraries with antibodies of the present invention; traditional cloning techniques using oligonucleotide probes of the present invention to screen appropriate libraries; and PCR amplification of appropriate libraries or DNA using oligonucleotide primers of the present invention. Preferred libraries to screen or from which to amplify nucleic acid molecules include Dirofilaria L3, L4 or adult cDNA libraries as well as genomic DNA libraries. Similarly, preferred DNA sources from which to amplify nucleic acid molecules include Dirofilaria L3, L4 or adult cDNA and genomic DNA. Techniques to clone and amplify genes are disclosed, for example, in Sambrook et al., ibid.

The present invention also includes nucleic acid molecules that are oligonucleotides capable of hybridizing, under stringent hybridization conditions, with complementary regions of other, preferably longer, nucleic acid molecules of the present invention such as those comprising Dirofilaria ADC nucleic acid molecules or other parasitic helminth ADC nucleic acid molecules. Oligonucleotides of the present invention can be RNA, DNA, or derivatives of either. The minimum size of such oligonucleotides is the size required for formation of a stable hybrid between an oligonucleotide and a complementary sequence on a nucleic acid molecule of the present invention. A preferred oligonucleotide of the present invention has a maximum size of preferably about 200 nucleotides, more preferably about 150 nucleotides and even more preferably about 100 nucleotides. The present invention includes oligonucleotides that can be used as, for example, probes to identify nucleic acid molecules, primers to produce nucleic acid molecules, or therapeutic reagents to inhibit parasitic helminth ADC protein production or activity (e.g., as antisense-, triplex formation-, ribozyme- and/or RNA drug-based reagents).

The present invention also includes the use of such oligonucleotides to protect animals from disease using one or more of such technologies. Appropriate oligonucleotide-containing therapeutic compositions can be administered to an animal using techniques known to those skilled in the art.

One embodiment of the present invention includes a recombinant vector, which includes at least one isolated nucleic acid molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid. Recombinant vectors can be used in the cloning, sequencing, and/or otherwise manipulating of parasitic helminth ADC nucleic acid molecules of the present invention.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, parasite, insect, other animal, and plant cells. Preferred expression vectors of the present invention can direct gene expression in bacterial, yeast, helminth or other parasite, insect and mammalian cells, and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, helminth or other endoparasite, or insect and mammalian cells, such as, but not limited to, tac, lac, trp, trc, oxy-pro, omp/lpp, rrnB, bacteriophage lambda (such as lambda PL and lambda PR and fusions that include such promoters), bacteriophage T7, T7lac, bacteriophage T3, bacteriophage SP6, bacteriophage SP01, metallothionein, alpha-mating factor, Pichia alcohol oxidase, alphavirus subgenomic promoter, antibiotic resistance gene, baculovirus, *Heliothis zea* insect virus, vaccinia virus, herpesvirus, raccoon poxyirus, other poxyirus, adenovirus, cytomegalovirus (such as immediate early promoter), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with parasitic helminths, such as *D immitis* transcription control sequences.

Suitable and preferred nucleic acid molecules to include in recombinant vectors of the present invention are as disclosed herein. Preferred nucleic acid molecules to include in recombinant vectors, and particularly in recombinant molecules, include $nDiADC_{456}$, $nDiADC_{475}$, $nDiADC_{517}$, $nDiADC_{808}$ and $nBmADC_{549}$.

Recombinant molecules of the present invention may also (a) contain secretory signals (i.e., signal segment nucleic acid sequences) to enable an expressed parasitic helminth protein of the present invention to be secreted from the cell that produces the protein and/or (b) contain fusion sequences which lead to the expression of nucleic acid molecules of the present invention as fusion proteins. Examples of suitable signal segments include any signal segment capable of directing the secretion of a protein of the present invention. Preferred signal segments include, but are not limited to, tissue plasminogen activator (t-PA), interferon, interleukin, growth hormone, histocompatibility and viral envelope glycoprotein signal segments. Suitable fusion segments encoded by fusion segment nucleic acids are disclosed herein. In addition, a nucleic acid molecule of the present invention can be joined to a fusion segment that directs the encoded protein to the proteosome, such as a ubiquitin fusion segment. Eukaryotic recombinant molecules may also include intervening and/or untranslated sequences surrounding and/or within the nucleic acid sequences of nucleic acid molecules of the present invention.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. It is to be noted that a cell line refers to any recombinant cell of the present invention that is not a transgenic animal. Transformed nucleic acid molecules of the present invention can remain extrachromosomal or can integrate into one or more sites within a chromosome of the transformed (i.e., recombinant) cell in such a manner that their ability to be expressed is retained. Preferred nucleic acid molecules with which to transform a cell include Dirofilaria and Brugia ADC nucleic acid molecules disclosed herein. Particularly preferred nucleic acid molecules with which to transform a cell include $nDiADC_{456}$, $nDiADC_{475}$, $nDiADC_{517}$, $nDiADC_{808}$ and $nBmADC_{549}$.

Suitable host cells to transform include any cell that can be transformed with a nucleic acid molecule of the present invention. Host cells can be either untransformed cells or cells that are already transformed with at least one nucleic acid molecule (e.g., nucleic acid molecules encoding one or more proteins of the present invention and/or other proteins useful in the production of multivalent vaccines). Host cells of the present invention either can be endogenously (i.e., naturally) capable of producing parasitic helminth ADC proteins of the present invention or can be capable of producing such proteins after being transformed with at least one nucleic acid molecule of the present invention. Host cells of the present invention can be any cell capable of producing at least one protein of the present invention, and include bacterial, fungal (including yeast), parasite (including helminth, protozoa and ectoparasite), other insect, other animal and plant cells. Preferred host cells include bacterial, mycobacterial, yeast, helminth, insect and mammalian cells. More preferred host cells include Salmonella, Escherichia, Bacillus, Listeria, Saccharomyces, Spodoptera, Mycobacteria, Trichoplusia, BHK (baby hamster kidney) cells, MDCK cells (Madin-Darby canine kidney cell line), CRFK cells (Crandell feline kidney cell line), CV-1 cells (African monkey kidney cell line used, for example, to culture raccoon poxyirus), COS (e.g., COS-7) cells, and Vero cells. Particularly preferred host cells are *Escherichia coli*, including *E. coli* K-12 derivatives; *Salmonella typhi*; *Salmonella typhimurium*, including attenuated strains such as UK-1 $_\chi$3987 and SR-11 $_\chi$4072; *Spodoptera frugiperda*; *Trichoplusia ni*; BHK cells; MDCK cells; CRFK cells; CV-1 cells; COS cells; Vero cells; and nontumorigenic mouse myoblast G8 cells (e.g., ATCC CRL 1246). Additional appropriate mammalian cell hosts include other kidney cell lines, other fibroblast cell lines (e.g., human, murine or chicken embryo fibroblast cell lines), myeloma cell lines, Chinese hamster ovary cells, mouse NIH/3T3 cells, LMTK$^{31}$ cells and/or HeLa cells. In one embodiment, the proteins may be expressed as heterologous proteins in myeloma cell lines employing immunoglobulin promoters.

A recombinant cell is preferably produced by transforming a host cell with one or more recombinant molecules, each comprising one or more nucleic acid molecules of the present invention operatively linked to an expression vector containing one or more transcription control sequences, examples of which are disclosed herein.

A recombinant cell of the present invention includes any cell transformed with at least one of any nucleic acid molecule of the present invention. Suitable and preferred nucleic acid molecules as well as suitable and preferred recombinant molecules with which to transfer cells are disclosed herein.

Recombinant cells of the present invention can also be co-transformed with one or more recombinant molecules including parasitic helminth ADC nucleic acid molecules encoding one or more proteins of the present invention and one or more other nucleic acid molecules encoding other protective compounds, as disclosed herein (e.g., to produce multivalent vaccines).

Recombinant DNA technologies can be used to improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant enzyme production during fermentation. The activity of an expressed recombinant protein of the present invention may be improved by fragmenting, modifying, or derivatizing nucleic acid molecules encoding such a protein.

Isolated parasitic helminth ADC proteins of the present invention can be produced in a variety of ways, including production and recovery of natural proteins, production and recovery of recombinant proteins, and chemical synthesis of the proteins. In one embodiment, an isolated protein of the present invention is produced by culturing a cell capable of expressing the protein under conditions effective to produce the protein, and recovering the protein. A preferred cell to culture is a recombinant cell of the present invention. Effective culture conditions include, but are not limited to, effective media, bioreactor, temperature, pH and oxygen conditions that permit protein production. An effective, medium refers to any medium in which a cell is cultured to produce a parasitic helminth ADC protein of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Examples of suitable conditions are included in the Examples section.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein", as well as similar phrases, refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for animals, for example, should exhibit no substantial toxicity and preferably should be capable of stimulating the production of antibodies in a treated animal.

The present invention also includes isolated (i.e., removed from their natural milieu) antibodies that selectively bind to a parasitic helminth ADC protein of the present invention or a mimetope thereof (e.g., anti-Dirofilaria ADC antibodies). As used herein, the term "selectively binds to" an ADC protein refers to the ability of antibodies of the present invention to preferentially bind to specified proteins and mimetopes thereof of the present invention. Binding can be measured using a variety of methods standard in the art including enzyme immunoassays (e.g., ELISA), immunoblot assays, etc.; see, for example, Sambrook et al., ibid., and Harlow, et al., 1988, *Antibodies, a Laboratory Manual*, Cold Spring Harbor Labs Press. An anti-ADC antibody of the present invention preferably selectively binds to a parasitic helminth ADC protein in such a way as to inhibit the function of that protein.

Isolated antibodies of the present invention can include antibodies in serum, or antibodies that have been purified to varying degrees. Antibodies of the present invention can be polyclonal or monoclonal, or can be functional equivalents such as antibody fragments and genetically-engineered antibodies, including single chain antibodies or chimeric antibodies that can bind to one or more epitopes.

A preferred method to produce antibodies of the present invention includes (a) administering to an animal an effective amount of a protein, peptide or mimetope thereof of the present invention to produce the antibodies and (b) recovering the antibodies. In another method, antibodies of the present invention are produced recombinantly using techniques as heretofore disclosed to produce ADC proteins of the present invention. Antibodies raised against defined proteins or mimetopes can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used (a) as therapeutic compounds to passively immunize an animal in order to protect the animal from parasitic helminths susceptible to treatment by such antibodies, (b) as reagents in assays to detect infection by such helminths and/or (c) as tools to screen expression libraries and/or to recover desired proteins of the present invention from a mixture of proteins and other contaminants. Furthermore, antibodies of the present invention can be used to target cytotoxic agents to parasitic helminths in order to directly kill such helminths. Targeting can be accomplished by conjugating (i.e., stably joining) such antibodies to the cytotoxic agents using techniques known to those skilled in the art. Suitable cytotoxic agents are known to those skilled in the art.

One embodiment of the present invention is a therapeutic composition that, when administered to an animal in an effective manner, is capable of protecting that animal from disease caused by a parasitic helminth. In one embodiment, therapeutic compositions of the present invention inhibit molting of larvae; i.e. reduce the ability of a larva to develop from one stage to the next, e.g. from L3 to L4. Therapeutic compositions of the present invention include at least one of the following protective compounds: an isolated parasitic helminth ADC protein or a mimetope thereof, an isolated parasitic helminth ADC nucleic acid molecule, an isolated antibody that selectively binds to a parasitic helminth ADC protein, an inhibitor of ADC function identified by its ability to bind to a parasitic helminth ADC protein and thereby impede development and/or migration of the parasite, and a mixture thereof (i.e., combination of at least two of the compounds). As used herein, a protective compound refers to a compound that, when administered to an animal in an effective manner, is able to treat, ameliorate, and/or prevent disease caused by a parasitic helminth. Preferred helminths to target are heretofore disclosed. Examples of proteins, nucleic acid molecules, antibodies and inhibitors of the present invention are disclosed herein.

The present invention also includes a therapeutic composition comprising at least one parasitic helminth ADC-based compound of the present invention in combination with at least one additional compound protective against one or more infectious agents. Examples of such compounds and infectious agents are disclosed herein.

Therapeutic compositions of the present invention can be administered to any animal susceptible to such therapy, preferably to mammals, and more preferably to dogs, cats, humans, ferrets, horses, cattle, sheep and other pets, economic food animals, work animals and/or zoo animals. Preferred animals to protect against heartworm disease include dogs, cats, humans and ferrets, with dogs and cats being particularly preferred. A preferred animal to protect against disease caused by parasitic helminths, for example elephantiasis, includes humans.

In one embodiment, a therapeutic composition of the present invention can be administered to the vector in which the parasitic helminth develops, such as to a mosquito in order to prevent the spread of heartworm. Such administration could be oral or by developing transgenic vectors capable of producing at least one therapeutic composition of the present invention. In another embodiment, an insect vector, such as a mosquito, can ingest therapeutic compositions present in the blood of a host that has been administered a therapeutic composition of the present invention.

In order to protect an animal from disease caused by a parasitic helminth, a therapeutic composition of the present invention is administered to the animal in an effective manner such that the composition is capable of protecting that animal from a disease caused by a parasitic helminth. Therapeutic compositions of the present invention can be administered to animals prior to infection in order to prevent infection (i.e., as a preventative vaccine) and/or can be administered to animals after infection in order to treat disease caused by the parasitic helminth (i.e., as a therapeutic vaccine).

Therapeutic compositions of the present invention can be formulated in an excipient that the animal to be treated can tolerate. Examples of such excipients include water, saline, Ringer's solution, dextrose solution, Hank's solution, and other aqueous physiologically balanced salt solutions. Non-aqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal,—or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, a therapeutic composition can include an adjuvant. Adjuvants are agents that are capable of enhancing the immune response of an animal to a specific antigen. Suitable adjuvants include, but are not limited to, cytokines, chemokines, and compounds that induce the production of cytokines and chemokines (e.g., granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I(IGIF), transforming growth factor beta, RANTES (regulated upon activation, normal T-cell expressed and presumably secreted), macrophage inflammatory proteins (e.g., MIP-1 alpha and MIP-1 beta), and Leishmania elongation initiating factor (LEIF)); bacterial components (e.g., endotoxins, in particular superantigens, exotoxins and cell wall components); aluminum-based salts; calcium-based salts; silica; polynucleotides; toxoids; serum proteins, viral coat proteins; block copolymer adjuvants (e.g., Hunter's Titermax™ adjuvant (Vaxcel™, Inc. Norcross, Ga.), Ribi adjuvants (Ribi ImmunoChem Research, Inc., Hamilton, Mont.); and saponins and their derivatives (e.g., Quil A (Superfos Biosector A/S, Denmark). Protein adjuvants of the present invention can be delivered in the form of the protein themselves or of nucleic acid molecules encoding such proteins using the methods described herein.

In one embodiment of the present invention, a therapeutic composition can include a carrier. Carriers include compounds that increase the half-life of a therapeutic composition in the treated animal. Suitable carriers include, but are not limited to, polymeric controlled release vehicles, biodegradable implants, liposomes, bacteria, viruses, other cells, oils, esters, and glycols.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ. Preferred controlled release formulations are biodegradable (i.e., bioerodible).

A preferred controlled release formulation of the present invention is capable of releasing a composition of the present invention into the blood of the treated animal at a constant rate sufficient to attain therapeutic dose levels of the composition to protect an animal from disease caused by parasitic helminths. The therapeutic composition is preferably released over a period of time ranging from about 1 to about 12 months. A controlled release formulation of the present invention is capable of effecting a treatment preferably for at least about 1 month, more preferably for at least about 3 months, even more preferably for at least about 6 months, even more preferably for at least about 9 months, and even more preferably for at least about 12 months.

Therapeutic compositions of the present invention can be administered to animals prior to infection in order to prevent infection and/or can be administered to animals after infection in order to treat disease caused by the parasitic helminth. For example, proteins, mimetopes thereof, and antibodies thereof can be used as immunotherapeutic agents. Acceptable protocols to administer therapeutic compositions in an effective manner include individual dose size, number of doses, frequency of dose administration, and mode of administration. Determination of such protocols can be accomplished by those skilled in the art. A suitable single dose is a dose that is capable of protecting an animal from disease when administered one or more times over a suitable time period. For example, a preferred single dose of a protein, mimetope or antibody therapeutic composition is from about 1 microgram (mg) to about 10 milligrams (mg) of the therapeutic composition per kilogram body weight of the animal. Booster vaccinations can be administered from about 2 weeks to several years after the original administration. Booster administrations preferably are administered when the immune response of the animal becomes insufficient to protect the animal from disease. A preferred administration schedule is one in which from about 10 $\mu$g to about 1 mg of the therapeutic composition per kg body weight of the animal is administered from about one to about two times over a time period of from about 2 weeks to about 12 months. Modes of administration can include, but are not limited to, subcutaneous, intradermal, intravenous, intranasal, oral, transdermal and intramuscular routes.

According to one embodiment, a nucleic acid molecule of the present invention can be administered to an animal in a fashion to enable expression of that nucleic acid molecule into a protective protein or protective RNA (e.g., antisense RNA, ribozyme, triple helix forms or RNA drug) in the animal. Nucleic acid molecules can be delivered to an animal in a variety of methods including, but not limited to, (a) administering a naked (i.e., not packaged in a viral coat or cellular membrane) nucleic acid as a genetic vaccine (e.g., as naked DNA or RNA molecules, such as is taught, for example in Wolff et al., 1990, Science 247, 1465–1468) or (b) administering a nucleic acid molecule packaged as a recombinant virus vaccine or as a recombinant cell vaccine (i.e., the nucleic acid molecule is delivered by a viral or cellular vehicle).

A genetic (i.e., naked nucleic acid) vaccine of the present invention includes a nucleic acid molecule of the present invention and preferably includes a recombinant molecule of the present invention that preferably is replication, or otherwise amplification, competent. A genetic vaccine of the present invention can comprise one or more nucleic acid molecules of the present invention in the form of, for example, a dicistronic recombinant molecule. Preferred genetic vaccines include at least a portion of a viral genome (i.e., a viral vector). Preferred viral vectors include those based on alphaviruses, poxyiruses, adenoviruses, herpesviruses, picornaviruses, and retroviruses, with those based on alphaviruses (such as sindbis or Semliki forest virus), species-specific herpesviruses and poxyiruses being particularly preferred. Any suitable transcription control sequence can be used, including those disclosed as suitable for protein production. Particularly preferred transcription control sequences include cytomegalovirus immediate early (preferably in conjunction with Intron-A), Rous sarcoma virus long terminal repeat, and tissue-specific transcription control sequences, as well as transcription control sequences endogenous to viral vectors if viral vectors are used. The incorporation of a "strong" polyadenylation signal is also preferred.

Genetic vaccines of the present invention can be administered in a variety of ways, with intramuscular, subcutaneous, intradermal, transdermal, intranasal and oral routes of administration being preferred. A preferred single dose of a genetic vaccine ranges from about 1 nanogram (ng) to about 600 $\mu$g, depending on the route of administration and/or method of delivery, as can be determined by those skilled in the art. Suitable delivery methods include, for example, by injection, as drops, aerosolized and/or topically. Genetic vaccines of the present invention can be contained in an aqueous excipient (e.g., phosphate buffered saline) alone or in a carrier (e.g., lipid-based vehicles).

A recombinant virus vaccine of the present invention includes a recombinant molecule of the present invention that is packaged in a viral coat and that can be expressed in an animal after administration. Preferably, the recombinant molecule is packaging- or replication-deficient and/or encodes an attenuated virus. A number of recombinant viruses can be used, including, but not limited to, those based on alphaviruses, poxyiruses, adenoviruses, herpesviruses, picomaviruses, and retroviruses. Preferred recombinant virus vaccines are those based on alphaviruses (such as Sindbis virus), raccoon poxyiruses, species-specific herpesviruses and species-specific poxyiruses. An example of methods to produce and use alphavirus recombinant virus vaccines are disclosed in PCT Publication No. WO 94/17813, by Xiong et al., published Aug. 18, 1994.

When administered to an animal, a recombinant virus vaccine of the present invention infects cells within the immunized animal and directs the production of a protective protein or RNA nucleic acid molecule that is capable of protecting the animal from disease caused by a parasitic helminth as disclosed herein. For example, a recombinant virus vaccine comprising an ADC nucleic acid molecule of the present invention is administered according to a protocol that results in the animal producing a sufficient immune response to protect itself from heartworm. A preferred single dose of a recombinant virus vaccine of the present invention is from about $1\times10^4$ to about $1\times10^8$ virus plaque forming units (pfu) per kilogram body weight of the animal. Administration protocols are similar to those described herein for protein-based vaccines, with subcutaneous, intramuscular, intranasal and oral administration routes being preferred.

A recombinant cell vaccine of the present invention includes recombinant cells of the present invention that express at least one protein of the present invention. Preferred recombinant cells for this embodiment include Salmonella, *E. coli*, Listeria, Mycobacterium, *S. frugiperda*, yeast, (including *Saccharomyces cerevisiae* and *Pichia pastoris*), BHK, CV-1, myoblast G8, COS (e.g., COS-7), Vero, MDCK and CRFK recombinant cells. Recombinant cell vaccines of the present invention can be administered in a variety of ways but have the advantage that they can be administered orally, preferably at doses ranging from about $10^8$ to about $10^{12}$ cells per kilogram body weight. Administration protocols are similar to those described herein for protein-based vaccines. Recombinant cell vaccines can comprise whole cells, cells stripped of cell walls or cell lysates.

The efficacy of a therapeutic composition of the present invention to protect an animal from disease caused by a parasitic helminth can be tested in a variety of ways including, but not limited to, detection of protective antibodies (using, for example, proteins or mimetopes of the present invention), detection of cellular immunity within the treated animal, or challenge of the treated animal with the parasitic helminth to determine whether the treated animal is resistant to disease. Challenge studies can include implantation of chambers including parasitic helminth larvae into the treated animal and/or direct administration of larvae to the treated animal. In one embodiment, therapeutic compositions can be tested in animal models such as mice. Such techniques are known to those skilled in the art.

One preferred embodiment of the present invention is the use of Dirofilaria ADC proteins, nucleic acid molecules, antibodies and inhibitors of the present invention, to protect an animal from heartworm. It is particularly preferred to prevent L3 that are delivered to the animal by the mosquito intermediate host from migrating from the site of inoculation and/or maturing into adult worms. As such, preferred therapeutic compositions are those that are able to inhibit at least one step in the portion of the parasite's development cycle that includes L3, third molt, L4, fourth molt, immature adult prior to entering the circulatory system. In dogs, this portion of the development cycle is about 70 days. Particularly preferred therapeutic compositions include *D. immitis* ADC-based therapeutic compositions of the present invention. Such compositions include *D. immitis* ADC nucleic acid molecules, *D. immitis* ADC proteins and mimetopes thereof, anti-*D. immitis* ADC antibodies, and inhibitors of *D. immitis* ADC function. Therapeutic compositions are administered to animals in a manner effective to protect the animals from heartworm. Additional protection may be obtained by administering additional protective compounds, including other parasitic helminth proteins, nucleic acid molecules, antibodies and inhibitory compounds, as disclosed herein.

One therapeutic composition of the present invention includes an inhibitor of parasitic helminth ADC function, i.e., a compound capable of substantially interfering with the function of a parasitic helminth ADC protein susceptible to inhibition. For example, an isolated protein or mimetope thereof is administered in an amount and manner that elicits (i.e., stimulates) an immune response that is sufficient, upon interaction with a native ADC protein, to protect the animal from the disease. Similarly, an antibody of the present invention, when administered to an animal in an effective manner, is administered in an amount so as to be present in the animal at a titer that is sufficient, upon interaction of that antibody with a native ADC protein, to protect the animal from the disease, at least temporarily. Oligonucleotide nucleic acid molecules of the present invention can also be administered in an effective manner, thereby reducing expression of parasitic helminth ADC proteins in order to interfere with development of parasitic helminths targeted in accordance with the present invention. Methods to identify certain functions, i.e., protein-binding capabilities, of parasitic helminth ADC proteins of the present invention are disclosed herein.

One embodiment of the present invention is a method to identify proteins that specifically interact with an ADC protein of the present invention. The method can comprise the steps of a) identifying and isolating a protein-binding domain of an isolated parasitic helminth ADC protein; b) contacting that protein-binding domain with isolated parasitic helminth proteins under conditions such that a parasitic helminth protein and the protein-binding domain can selectively interact and/or bind to each other, using, for example, the yeast two-hybrid system see, for example, Luban, et al., 1995, *Curr. Opin. Biotechnol.*, 6, 59–64; and c) identifying those proteins that specifically bind to the isolated ADC protein-binding domain. Additional methods to identify protein—protein interactions with the protein-binding domains of an isolated ADC protein of the present invention are known to those skilled in the art. Examples include Biacore® screening, confocal immunofluorescent microscopy, and immunoprecipitations.

An inhibitor of ADC function can be identified using parasitic helminth ADC proteins of the present invention. A preferred inhibitor of ADC function is a compound capable of substantially interfering with the function of a parasitic helminth ADC protein and which does not substantially interfere with host animal ADC activity. As used herein, a compound that does not substantially inhibit host animal aromatic amino acid decarboxylase activity is one that, when administered to a host animal, the host animal shows no significant adverse effects attributable to the compound and which, when administered to an animal in an effective manner, is capable of protecting that animal from disease caused by a parasitic nematode.

A preferred method to identify a compound capable of inhibiting filariid aromatic amino acid decarboxylase activity includes contacting an isolated filariid aromatic amino acid decarboxylase protein having an amino acid sequence selected from the group consisting of SEQ ID NO:6, SEQ ID NO:10, SEQ ID NO:14, SEQ ID NO:17, and SEQ ID NO:20 with a putative inhibitory compound under conditions in which, in the absence of said compound, said protein has aromatic amino acid decarboxylase activity; and determining if said putative inhibitory compound inhibits said activity. An additional preferred method of identifying a compound capable of inhibiting filariid aromatic amino acid decarboxylase activity includes contacting an isolated host animal aromatic amino acid decarboxylase protein with the putative filariid aromatic amino acid decarboxylase inhibitory compound under conditions in which, in the absence of said compound, said host animal aromatic amino acid decarboxylase protein has aromatic amino acid decarboxylase activity; and determining if said putative inhibitory compound inhibits the host animal aromatic amino acid decarboxylase activity.

Another embodiment of the present invention is a method to identify a compound capable of inhibiting ADC function of a parasitic helminth. Such a method includes the steps of: (a) identifying a protein binding or regulatory activity of an isolated ADC protein in vitro; (b) identifying a putative compound capable of binding to and/or inhibiting the identified protein binding or regulatory activity of the isolated ADC protein; (c) contacting D. immitis L3 larvae with the putative inhibitory compound under conditions in which, in the absence of the compound, the larvae are able to molt to the L4 stage; and (d) determining if the putative compound inhibits molting. Putative inhibitory compounds to screen include small organic molecules, antibodies (including mimetopes thereof), and ligand analogs. Such compounds are also screened to identify those that are substantially not toxic in host animals.

Inhibitors of ADC function identified by such a method can be tested for their ability to block development and/or migration of parasitic helminths, and particularly of D. immitis in vivo. Preferred ADC proteins to inhibit are those produced by parasitic helminths as disclosed herein. A preferred inhibitor of the present invention is capable of protecting an animal from disease caused by parasitic helminths. Compositions comprising inhibitors of ADC function can be administered to animals in an effective manner to protect animals from disease caused by parasitic helminths. Effective amounts and dosing regimens can be determined using techniques known to those skilled in the art.

It is also within the scope of the present invention to use isolated proteins, mimetopes, nucleic acid molecules and antibodies of the present invention as diagnostic reagents to detect infection by parasitic helminths. Such diagnostic reagents can be supplemented with additional compounds that can specifically detect all phases of the parasite's life cycle. Methods to use such diagnostic reagents to diagnose parasitic helminth infection are well known to those skilled in the art. Suitable and preferred parasitic helminths to detect are those to which therapeutic compositions of the present invention are targeted. Preferred parasitic helminths to detect using diagnostic reagents of the present invention are D. immitis and B. malayi.

One embodiment of the present invention is a method for detecting the presence of an amino acid decarboxylase. This method, which is described in greater detail in the Examples below, includes the steps of (a) contacting a putative amino acid decarboxylase-containing composition with a synthetic substrate to create a reaction product, wherein the synthetic substrate comprises an amino acid conjugated to a tag which produces a reference signal, where the tag is cleaved from the synthetic substrate in the presence of an amino acid decarboxylase resulting in a cleavage product which produces a cleavage signal which is different from the reference signal; and (b) observing the reaction signal produced by the reaction product and comparing the reaction signal with the reference signal and the cleavage signal. A reaction signal qualitatively equivalent to the cleavage signal indicates the presence of an amino acid decarboxylase.

As used herein, a tag is any detectable marker, including, but not limited to a molecule which has fluorescent and/or calorimetric properties, chemiluminescent properties, and radioactivity and which may be conjugated to a substrate. As used herein, a putative amino acid decarboxylase-containing composition may include any biological or chemical sample, whether in a purified or unpurified state, including but not limited to blood, serum, tissues, and other bodily fluids. As used herein, a signal includes any detectable signal, including but not limited to fluorescence, chemiluminescence, and a colorimetric signal, and as such, may be measured by methods know to those of skill in the art such as fluoroscopy, light spectroscopy and autoradiography. Examples of compounds having signals which are qualitatively equivalent include, but are not limited to, compounds which have essentially the same emission wavelength as measured by fluorescence spectroscopy, compounds which exhibit essentially the same color or compounds which elute at essentially the same size when separated by electrophoresis.

In one embodiment of the present invention, a preferred tag for use in a method for detecting the presence of an amino acid decarboxylase is a detectable marker which has different fluorescent or calorimetric properties when conjugated to a substrate compared to when the tag is not conjugated to a substrate. A preferred tag of the present invention includes, but is not limited to 7-amido-4-methylcoumarin, 4-methylcoumarin, 2-Naphthylamine 4-Methoxy-2-Naphthylamine, o-Phthalaldehyde, Cresyl Violet, 5-Nitrosalicylaldehyde, 7-Hydroxy-4-Trifluoromethylcoumarin, Rhodamine 110, Naphthyl AS-MX, 7-Amino-4-Trifluoromethylquinolone, Naphthyl AS-TR, 5,5'-Dithio-bis-2-Nitrobenzoic acid, 6-Amino-2Quinolone, 6-Amino-2-Styrylquinoline, 4-Nitroanilide, 5-Aminoisopohthalic Acid Dimethyl Esther, 4-Methylumbelliferone, Naphthyl AS-BI, and derivatives and substituted forms thereof. A particularly preferred fluorescent tag is 7-amido-4-methylcoumarin (AMC).

A preferred substrate for use in a method for detecting the presence of an amino acid decarboxylase is an amino acid residue conjugated to a tag (i.e. a conjugated amino acid substrate) to form a compound having the formula:

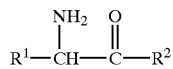

As used herein, a conjugated amino acid substrate may include one or more contiguous amino acid residues.

In one embodiment of the present invention, a preferred substrate for use in a method for detecting the presence of an amino acid decarboxylase has the formula:

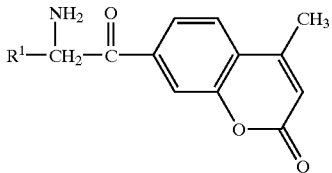

In one embodiment of the present invention, a preferred substrate for use in a method for detecting the presence of an amino acid decarboxylase is an amino acid residue conjugated to AMC having the formula:

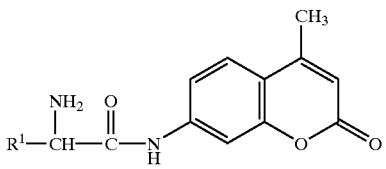

with phenylalanine conjugated AMC, tyrosine conjugated AMC and tryptophan conjugated AMC being particularly preferred.

Preferred enzymes to detect are amino acid decarboxylases with phenylalanine decarboxylase, tyrosine decarboxylase and tryptophan decarboxylase being particularly preferred. A preferred sample from which to detect an amino acid decarboxylase includes a sample from an animal, with a sample from a mammal being preferred and with a sample from a human, dog, cat, or a horse being particularly preferred.

The following examples are provided for the purposes of illustration and are not intended to limit the scope of the present invention.

EXAMPLES

Example 1

This example describes the characterization of an enzyme from *Dirofilaria immitis*.

The present invention includes the surprising discovery that the ability of *D. immitis* L3/L4 larvae excretory/secretory product (ES) and whole adult *D. immitis* extract to cleave the synthetic amino acid substrate H-Phe-AMC as reported by Richer et al. 1992, *Exper. Parasitol.*, 75:213–222 and thought to be due to a metallo-aminopeptidase, is due to *D. immitis* aromatic amino acid decarboxylases (Di-ADC) present in *D. immitis* L3/L4 ES and in adult *D. immitis* extract. Further purification and characterization of this enzyme is described in greater detail in Examples 2–4. Initially, *D. immitis* L3/L4 ES was tested for the ability to cleave a variety of fluorescent tag conjugated synthetic substrates, wherein cleavage is determined by detecting tag released after mixing enzyme and substrate. After establishing which substrates were cleaved by a component of *D. immitis* L3/L4 ES, the effects of various known protease inhibitors on this activity were determined by incubating the enzyme with each inhibitor and with a tagged substrate, which Di-ADC would normally cleave in the absence of the inhibitor, and measuring the released fluorescent tag as described above. The resulting profile of substrate specificity and inhibition was found to be characteristic of an aromatic amino acid decarboxylase.

A. *D. immitis* L3/L4 ES, prepared as described in U.S. Pat. No. 5,639,876, was tested for protease-like activity against sixteen synthetic substrates, listed in Table I conjugated to a fluorescent tag, 7-amido-4-methylcoumarin (AMC), (conjugate substrates available from Sigma Chemical, St. Louis, Mo. and Bachem California Inc., Torrance, Calif.). Thirteen of these substrates were single amino acid residues, two contained an internal phenylalanine residue, used to distinguish aminopeptidase from endopeptidase activity, and one was a substrate specific for cysteine proteases. Reactions were started by adding individual substrates to a final concentration of 0.05 millimolar (mM) to 25 micrograms ($\mu$g) of *D. immitis* L3/L4 ES dissolved in 100 microliters ($\mu$L) pH 7.5 phosphate-buffered saline (PBS), containing 0.005% Brij35 in a 96-well microfluor plate (available from Dynatech Laboratories Inc., Chantilly, Va.). Enzyme activity in a given sample is indicated by the release of AMC, which fluoresces at different emission wavelengths when in a conjugated versus an unconjugated state, as measured with a luminescence spectrometer, e.g. model LS 50B, available from Perkin Elmer, Norwalk, Conn. The release of AMC was determined herein by measuring the change of absorption at $\lambda_{Ex}/\lambda_{Em}$= 380 nm/460 nm, wherein $\lambda_{Ex}$ represents the excitation wavelength in nanometers (nm) and $\lambda_{Em}$ represents the emission wavelength, unless otherwise noted.

The results, summarized in Table I, indicate that a component of *D. immitis* L3/L4 ES specifically cleaves aromatic amino acid substrates, does not have endopeptidase activity and does not cleave substrates specific for cysteine proteases under the described conditions. A similar assay was performed using Di-ADC extracts from adult male and female *D. immitis* purified by Mono-Q chromatography as described in Example 2. Di-ADC purified from whole adult homogenates had the same substrate specificity as Di-ADC purified from *D. immitis* L3/L4 ES.

TABLE I

Substrate specificity of *D. immitis* L3/L4 ES

| Substrates | *D. immitis* L3/L4 ES Activity |
|---|---|
| H—Gly—AMC | No |
| H—Ala—AMC | No |
| H—Leu—AMC | No |
| H—Ser—AMC | No |
| H—Phe—AMC | Yes |
| H—Tyr—AMC | Yes |
| H—Trp—AMC | Yes |
| H—Met—NHNap | No |
| H—Pro—AMC | No |
| H—Glu—AMC | No |
| H—Lys—AMC | No |
| H—Arg—AMC | No |
| H—His—AMC | No |
| Glutaryl—Phe—AMC | No |
| Ala—Ala—Phe—AMC | No |
| Z—Val—Leu—Arg—AMC | No |

B. The effect of inhibitors on the ability of Di-ADC to cleave the synthetic substrate H-Phe-AMC was tested as follows. *D. immitis* L3/L4 ES was pre-incubated in 100 $\mu$L PBS pH 7.5 containing 0.005% Brij35 in a 96-well plate for 30 minutes at 37° C. with individual inhibitors, available from Sigma Chemical, St. Louis Mo. and Boehringer-Mannheim, Indianapolis, Ind., at the concentrations indicated in Table II. Reactions were started by adding H-Phe-AMC to a final concentration of 50 millimolar (mM). The change of absorption at $\lambda_{Ex}/\lambda_{Em}$=380 nm/$\lambda_{460}$ nm was recorded as described in section A at 5 minute intervals for the first 15 minutes, at 15 minute intervals for the next hour and at 30 minute intervals for up to 6 hours after the start of the reaction.

TABLE II

Inhibitors tested against the protease activity from *D. immitis* L3/L4 ES.

| INHIBITOR | INHIBITOR CONCENTRATION |
|---|---|
| Amstatin | 10 μM |
| Bestatin | 10 μM |
| Actinonin | 50 μg/ml |
| Phosphoramidon | 10 μM |
| N-ethylmaleimide (NEM) | 500 μg/ml |
| Puromycin | 50 μg/ml |
| 1,10-Phenanthroline | 10 mM |
| 1,7-Phenanthroline | 10 mM |
| p-Aminobenzoyl-G—P-dL-dA-Hydroxam Acid | 50 μg/ml |
| Ethylenediaminetetraacetic acid (EDTA) | 10 mM |
| Diprotin A (H—I—P—I—OH) | 50 μM |
| Diprotin B (H—V—P—L—OH) | 100 μM |
| 3,4-Dichioroisocoumarin (3,4-DCI) | 100 μM |
| E-64 | 10 μM |
| Phenylmethane-7-sulfonyl fluoride(PMSF) | 1 mM |
| Diisopropyl fluorophosphate (DFP) | 0.1 mM |
| Pefabloc | 4 mM |
| 5-hyroxytryptamine (5-HT; Serotonin) | 4 mM |
| p-chloromercuribenzoic acid | 0.4 mM |
| Semicarbazide | 0.4 mM |

The results, summarized in FIG. 1, indicate that the activity of the enzyme is sensitive to some serine protease inhibitors (i.e Pefabloc, PMSF and 3,4-DCI) and is not sensitive to the other inhibitors tested, including aminopeptidase inhibitors. The same inhibition assay was carried out using Mono-Q chromatography purified Di-ADC from adult *D. immitis* homogenates, purified as described in Example 2, as the enzyme source. The results of that assay indicate that the adult enzyme has the same inhibitor profile as the *D. immitis* L3/L4 ES.

Example 2

This example describes the purification and further characterization of a Di-ADC. Also disclosed is the N-terminal amino acid sequence of an aromatic amino acid decarboxylase purified from adult *D. immitis*.

Purification and partial characterization of a novel Di-ADC was carried out as follows. All operations were performed at 4° C. unless otherwise mentioned. About fifteen grams of adult *D. immitis*, male and female, were ground in liquid nitrogen and homogenized in 200 ml pH 7.5 PBS followed by sonication on ice with standard ½ inch disrupter horns three times for 15 seconds at 2 second cycle, 50% duty cycle and output control 5 using a Sonicator W-380, available from Heat Systems-Ultrasonics Inc., Formingdale, N.Y. The resulting homogenate was centrifuged at 20,000× g for 30 minutes at 4° C. The protein concentration of the resulting supernatant was determined by microplate assay using Bio-Rad protein assay reagent, available from Bio-Rad Laboratories, Hercules, Calif., to be 2 milligrams per milliliter (mg/ml). The supernatant was fractionated by Mono-Q chromatography with the Bio-Rad Biologic Chromatography System using a linear gradient of 0% to 80% 1 molar (M), pH 8.5 NaCl in 50 mM Tris buffer. Each fraction off the Mono-Q column was monitored for the ability to cleave an H-Phe-AMC substrate as described in Example 1. Each reaction was started by adding 0.05 mM (final concentration) of H-Phe-AMC substrate to 25 μg of individual *D. immitis* fractions dissolved in pH 7.5 PBS containing 0.005% Brij35. The enzyme activity of each reaction was measured by detection of released AMC as described in Example 1. Fractions which were positive for enzyme activity were recombined and precipitated with 4 M $(NH_4)_2SO_4$ and redissovled in 1 M, pH 7.5 $(NH_4)_2SO_4$ phosphate buffer. The protein concentration of the recombined fractions was determined to be 0.5 mg/ml. The resulting sample was further separated on a hydrophobic interaction column (HIC) with the Bio-Rad Biologic System using 1 M $(NH_4)_2SO_4$ in 20 mM $PO_4$ buffer and Di-ADC activity in the resulting fractions was monitored as described in Example 1. Fractions which were positive for Di-ADC activity were recombined and precipitated with 4 M $(NH_4)_2SO_4$. The protein concentration of the recombined fractions was determined to be 0.041 mg/ml. The recombined fraction were further purified by gel filtration chromatography, using pH 7.5 PBS. Fractions containing Di-ADC activity were recombined and the protein concentration was determined to be 0.045 mg/ml.

Further purification was performed by preparative isoelectrofocusing (IEF) which demonstrated that the protein with Di-ADC activity has a pI of about 5.6. Protein from the IEF gel was eluted using a Bio-Rad whole gel elutor according to the manufacturer's instructions. The fraction eluted from the IEF gel containing peak enzyme activity was separated by sodium dodecyl sulfate polyacrylamide gel electrophoresis (SDS-PAGE) and silver stained to reveal a primary protein band having an approximate weight of 48 kilodaltons (kDa) and minor bands having approximate weights of 35 kDa.

Proteins separated by SDS-PAGE after IEF were transferred to a polyvinylidene difluoride (PVDF) membrane and stained with Coomassie Blue. The protein band of 48 kDa was isolated for N-terminal amino acid sequencing. Four separate sequencing runs were conducted on the 48 kDa protein using standard procedures known to those in the art (see, for example, Geisow et al., 1989, in *Protein Sequencing: A Practical Approach*, J B C Findlay and M J Geisow (eds.), IRL Press, Oxford, England, pp. 85–98; Hewick et al., 1981, *J. Biol. Chem.*, 256:7990–7997) to yield a putative 20-amino acid consensus sequence of QLYIKQVQVQKRQEKIEYQV, denoted herein as SEQ ID NO:1.

A homology search of a non-redundant protein database was performed on SEQ ID NO:1 through the National Center for Biotechnology Information (NCBI), National Library of Medicine, National Institute of Health, Baltimore, Md., using the BLAST network. This database includes SwissProt+PIR+SPupdate+GenPept+GPUpdate+PDB databases. The highest scoring match of the homology search at the amino acid level was GenBank™ accession #1836071, a *Bacillus pumilus* ferulic acid decarboxylase which was 30% identical over a 15 amino acid stretch to SEQ ID NO:1.

Example 3

This example describes experiments comparing the properties of Di-ADC to commercially prepared aromatic amino acid decarboxylases.

A. A substrate specificity assay was performed on commercially prepared phenylalanine decarboxylase (Phe-DC) and tyrosine decarboxylase (Tyr-DC), available from Sigma Chemical, in a manner similar to that performed with Di-ADC described in Example 1, using the substrates listed in Table I, except H-Met-NHNap, Ala-Ala-Phe-AMC and Z-Val-Leu-Arg-AMC were not used. Phe-DC and Tyr-DC were each shown to cleave H-Phe-AMC, Trp-DC and H-Tyr-AMC.

The inhibitor assay described in Example 1 was repeated using commercially prepared Phe-DC and Tyr-DC as the enzyme source. The inhibitors used included the protease inhibitors Pefabloc, DFP, PMSF and 3,4 DCI and reported ADC inhibitors p-chloromercuribenzoic acid (CMBA) and 5-hydroxytryptamine (5-HT). Pefabloc, DFP, CMBA and 5-HT inhibited Phe-DC and Tyr-DC activity at levels similar to the level that each inhibited Di-ADC. PMSF and 3,4 DCI inhibited Di-ADC activity more strongly than they inhibited either Phe-DC or Tyr-DC activity.

B. The following experiment demonstrated that Di-ADC cleaves a phenylalanine substrate by decarboxylation, as shown by carbon dioxide release upon cleavage, rather than by an alternative mechanism. A carbon dioxide detection kit, INFINITY™ $CO_2$, available from Sigma Chemical, was used to detect carbon dioxide production as a result of Di-ADC activity as follows. Partially purified adult Di-ADC, purified as described in Example 2 through the gel filtration chromatography step, was mixed in 5 µL, 10 µL and 20 µL reactions with 5 mM final concentration of L-phenylalanine in 50 µl of pH 7.5 PBS containing 0.005% Brij35 at 37° C. for 45 minutes in a sealed microplate. At the end of the reaction, 10 µl of reaction mixture was added to 300 µl of INFINITY $CO_2$ solution and incubated for an additional 10 minutes at room temperature. The absorption change at 380 nm was measured with a spectrophotometer and the $CO_2$ formation during decarboxylation was calculated therefrom. Formation of 0.7, 0.38 and 0.4 mM of $CO_2$ was detected in the reaction mixture of 5 µL, 10 µL and 20 µl Di-ADC respectively. A control reaction which used 375 U of commercially prepared Phe-DC as the enzyme produced 0.27 mM of $CO_2$.

C. Thin layer chromatography (TLC) was used to identify the substrate cleavage site of H-Phe-AMC by Di-ADC. Chymotrypsin, Phe-DC and Di-ADC were reacted with an H-Phe-AMC substrate as described in Example 1. The end products from these reactions were purified with 100% chloroform and fractionated on a silica TLC plate (Silica gel 60, available from Merck & CO., Inc., Whitehouse Station, N.J.) which had been impregnated with 5% Tris base and air dried. The solvent used was toluene/acetone (23/7). Pure AMC was used as a control. A second TLC was run with the H-Phe-AMC reaction product and pure AMC and stained with ninhydrin spray reagent (available from Sigma). Ninhydrin detects HOOC-AMC but does not detect AMC.

Analysis of the migration distance of the reaction products indicated the following: an end product from the chymotrypsin reaction was similar in size to pure AMC; and an end product of the Di-ADC reaction was similar in size to an end product of the Phe-DC reaction end product, both of which were smaller than pure AMC. The ninhydrin-stained TLC plate revealed a ninhydrin-stained product in the H-Phe-AMC reaction, but did not stain the pure AMC. Since ninhydrin revealed a spot in the H-Phe-AMC reaction, the end product of the reaction is HOOC-AMC, and not pure AMC which would not have been detected. This study thus demonstrated that Di-ADC cleaved H-Phe-AMC at the same site as commercially prepared Phe-DC and that this cleavage site was different from that of chymotrypsin.

D. Excitation and emission wavelengths of a given chemical can be used as a physical "fingerprint" for that chemical. Reactions of Di-ADC, Phe-DC and chymotrypsin with an H-Phe-AMC substrate were conducted as described in Example 1 and the excitation and emission wavelengths of the end products were measured using a luminescence spectrometer. Pure AMC was measured as a control.

The $\lambda_{Ex}/\lambda_{Em}$ for the fluorescent end products from the Di-ADC and Phe-DC reactions were 344/425 while those from the chymotrypsin reaction and the pure AMC control were 343/441. This result indicates that both Di-ADC and Phe-DC cleave the substrate at the decarboxylase cleavage site to produce HOOC-AMC whereas chymotrypsin cleaves the substrate at the aminopeptidase cleavage site to produce AMC. The location of these cleavage sites and the end products resulting from each type of cleavage are illustrated as follows:

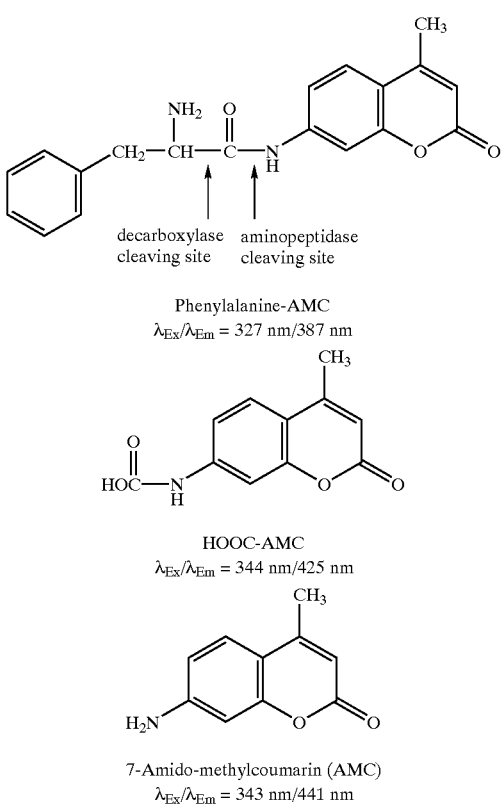

Phenylalanine-AMC
$\lambda_{Ex}/\lambda_{Em}$ = 327 nm/387 nm

HOOC-AMC
$\lambda_{Ex}/\lambda_{Em}$ = 344 nm/425 nm

7-Amido-methylcoumarin (AMC)
$\lambda_{Ex}/\lambda_{Em}$ = 343 nm/441 nm

E. Enzyme kinetics, as measured by Michaelis constant ($K_m$) and maximal velocity ($V_{max}$), can be used to characterize the activity of an enzyme towards a given substrate under defined conditions. Enzymatic reactions were performed under the fluorimetric assay conditions described in Example 1 using Di-ADC and commercially prepared Phe-DC as the enzymes and H-Phe-AMC, H-Tyr-AMC and H-Trp-AMC as the substrates. One µL of purified adult Di-ADC, prepared as described in Example 2 through the gel filtration chromatography step, or 80 micro units (µU) (11.4 µg) of Phe-DC were incubated with each substrate at substrate concentrations ranging from 0.0016 to 0.2 mM. Each reaction was carried out in duplicate in PBS reaction buffer and monitored using the fluorimetric method described in Example 1. The values of apparent $K_m$ and $V_m$, of Di-ADC and Phe-DC for the substrates H-Phe-AMC, H-Tyr-AMC and H-Trp-AMC were calculated from a double-reciprocal plot of 1/v against 1/[substrate].

The resulting $K_m$ values of Di-ADC, shown in µM, and $V_{max}$ values, shown in pico moles per milligram per minute (pmol/mg/min), summarized in Table III, are similar to those derived for Phe-DC, further indicating that Di-ADC is an aromatic amino acid decarboxylase.

TABLE III

|  | Di-ADC | | Phe-DC | |
| --- | --- | --- | --- | --- |
|  | Km (μM) | Vmax | Km (μM) | Vmax |
| H—Phe—AMC | 32.1 | 0.234 | 23.1 | 0.619 |
| H—Tyr—AMC | 35.1 | 0.152 | 72.3 | 0.339 |
| H—Trp—AMC | 29.1 | 0.140 | 22.9 | 0.703 |

Example 4

This example describes the characterization of *D. immitis* aromatic amino acid decarboxylase (Di-ADC) activity by measuring the ability of Di-ADC to catalyze the formation of dopamine from dopa.

The ability to catalyze the formation of dopamine from dopa has been described as a classical method for identifying aromatic amino acid decarboxylases, see for example, Carla Borri Voltattomi et al. 1987, *Methods in Enzymology*, 142:179–187. In order to confirm that Di-ADC is an aromatic amino acid decarboxylase, an assay was carried out to measure the ability of Di-ADC to catalyze the formation of dopamine from dopa. Commercially prepared Phe-DC, available from Sigma Chemical was used as the control in the investigation. Reactions were carried out by incubating 10 μl of Di-ADC, purified as described in Example 2 through the gel filtration chromatography step or 172 μU Phe-DC in 100 μl pH 7.5 PBS, containing 0.005% Brij35 and 0.5 mM L-dopa, available from Sigma Chemical, at 37° C. for 30 minutes. The reactions were stopped by incubating the reactions at 100° C. for 1 minute. One ml of benzene and 1 ml of 2,4,6-trinitrobenzene-1-sulfonic acid (0.126% in PBS) were added to each reaction and incubated at 42° C. for 1 hour with continuous shaking to extract formed dopamine into the benzene layer and convert the formed dopamine into trinitrophenyl-1-dopamine.

The formation of trinitrophenyl-1-dopamine from dopamine (and hence the formation of dopamine from dopa) was measured in a spectrophotometer using $\epsilon_{340\ nm}$=12,400 $M^{-1}$ $cm^{-1}$. In this assay, Phe-DC formed 9.4 nmol of dopamine and Di-ADC formed 2.74 nmol of dopamine, demonstrating once again that Di-ADC is an aromatic amino acid decarboxylase.

The role of Di-ADC in catalyzing the formation of dopamine from dopa was further shown by demonstrating the effects of various inhibitors upon the conversion of dopa to dopamine. Three separate Phe-DC and Di-ADC reactions were prepared as described above and three Tyr-DC reactions were similarly prepared using 25 μU of Tyr-DC to provide an additional control. Three inhibitors, CMBA, Pefabloc and DFP, were separately pre-incubated for 30 min at 37° C. with each of the three enzymes in 90 μl reaction buffer as described in Example 1. L-dopa was added to each reaction at a final concentration of 0.5 mM and incubated for another 30 min at 37° C. Following the incubation with L-dopa, each reaction was stopped, the dopamine was extracted and dopamine formation was measured. The effect of the inhibitors upon the formation of dopamine from L-dopa followed a profile matching the inhibitor profile for the ability of Di-ADC to cleave aromatic amino acid substrates described in Examples 1 and 3, further indicating that Di-ADC is an aromatic amino acid decarboxylase.

Example 5

This example describes the isolation and sequencing of nucleic acid molecules encoding *D. immitis* aromatic amino acid decarboxylase proteins of the present invention.

A. A Di-ADC nucleic acid molecule of about 456-bp was isolated from adult *D. immitis* first strand cDNA (reverse transcribed from adult *D. immitis* mRNA) by PCR amplification as follows. Initially, primers were designed using sequences from a putative ADC-like nucleic acid molecule from *Caenorhabditis elegans*. These initial attempts to PCR-amplify an ADC related nucleic acid molecule from *D. immitis* using standard PCR amplification conditions and *C. elegans*-derived primers were unsuccessful.

B. In another attempt, degenerate PCR primers were designed based on three conserved regions of a putative *C. elegans* ADC-like nucleic acid molecule. These primers included forward primers CEADC243FD and CEADC327FD having, respectively, the nucleotide sequences 5' TTY CAY GCN TAY TTY CCN GCN GGN AAY 3', denoted herein as SEQ ID NO:2, and 5' TGG GCN GCN TGY CCN GCN ATG ACN GAR CTN GAR 3', denoted herein as SEQ ID NO:22, and two reverse primers CEADC890RD and CEADC1200RD, having, respectively, the nucleotide sequences 5' RTA NGC NGC RTC NAC RTG NAR CCA 3', denoted herein as SEQ ID NO:3, and 5' ACR AAC CAN ARY TTN ARN CWN CKR AAN CKN $C_3$', denoted herein as SEQ ID NO:4. These degenerate *C. elegans*-derived primers were used in a modified amplification procedure called "touchdown" PCR in order to amplify *D. immitis* ADC nucleic acid molecules. Touchdown PCR was used in all PCR amplifications described below unless otherwise noted. This procedure included the following amplification cycles: (1) one cycle of 94° C. for 8 min; (2) three cycles of 94° C. for 30 sec, 58° C. for 45 sec, and 72° C. for 1 min; (3) seven sets of three cycles each wherein denaturation temperature was 94° C. for 30 sec and extension temperature was 72° C. for 1 min but annealing temperature decreased by two degrees between sets, from 58° C. for the initial set to 46° C. for the final set for a total of 21 cycles) and (4) 25 cycles of 94° C. for 30 sec, 44° C. for 45 sec, and 72° C. for 1 min.

C. A first PCR amplification was carried out using primers with SEQ ID NO:2 and SEQ ID NO:4 and adult *D. immitis* first strand cDNA as the template. The product of this first PCR reaction was used as the template in a second PCR amplification using primers with SEQ ID NO:22 and SEQ ID NO:3. The product of the second amplification was purified by agarose gel electrophoresis to yield a 456-bp DNA fragment, denoted herein as $nDiADC_{456}$. This fragment and *D. immitis* and *B. malayi* nucleic acid molecules hereinafter described reflect the size and sequence of the molecule with *C. elegans* derived primers removed. Southern blot hybridization under low stringency conditions, using 0.5× Sodium Chloride Sodium Citrate buffer (SSC), 0.1% SDS at 42° C., (1× SSC contains 0.15 M Sodium Chloride and 0.015 M Sodium Citrate) revealed that $nDiADC_{456}$ could bind under those conditions to *C. elegans* ADC-like sequence, EMBL Accession # Z49068.

The PCR-amplified fragment containing $nDiADC_{456}$ was excised from the gel and purified using a QIAquick™ kit, available from Qiagen, Chatsworth, Calif., according to the manufacturer's instructions. The resultant 456-bp DNA fragment was subcloned into the pCRII TA™ vector, available from Invitrogen, San Diego, Calif., according to the manufacturer's instructions.

The nucleic acid molecule $nDiADC_{456}$ was sequenced by the Sanger dideoxy chain termination method, using the PRISM™ Ready Dye Terminator Cycle Sequencing Kit with AmpliTaq™ DNA Polymerase, FS, available from Perkin-Elmer Corporation. PCR extensions were done in the GeneAmp™ PCR System 9600, available from Perkin- Elmer. Excess dye terminators were removed from extension products using the Centriflex™ Gel Filtration Cartridge, available from Advanced Genetics Technologies Corporation, Gaithersburg, Md., following the standard protocol. Samples were resuspended according to manufacturer's protocols and were run on a Perkin-Elmer ABI PRISM™ 377 Automated DNA Sequencer. The resulting nucleic acid sequence of nDiADC$_{456}$ has a coding strand presented herein as SEQ ID NO:5 and a complementary strand presented herein as SEQ ID NO:7.

Translation of SEQ ID NO:5 yields a protein of about 152 amino acids, denoted herein as PDiADC$_{152}$, the amino acid sequence of which is presented in SEQ ID NO:6, assuming a first in-frame codon extending from nucleotide 1 to nucleotide 3 of SEQ ID NO:5.

Homology searches was performed on SEQ ID NO:5 and SEQ ID NO:6, using the blastn and blastp programs, respectively, available through the BLAST network of the NCBI. The highest scoring match of the homology search at the nucleotide level was *C. elegans* putative ADC-like nucleic acid molecule, EMBL Accession number Z49068. Information available through NCBI for this sequence includes the location of computer predicted introns. Intron location information was used by Applicants to predict the sequence of a 1770-bp *C. elegans* cDNA molecule encoding a putative *C. elegans* ADC-like protein. This computer predicted *C. elegans* sequence was compared to SEQ ID NO:5 using the Compare function by maximum matching within the program DNAsis Version 2.1 using default parameters. These parameters revealed a 66.8% identity over 456 nucleotides. The highest scoring match at the amino acid level was to *C. elegans* putative ADC-like protein, EMBL Accession No. 780197, with 84.8% identity over 152 amino acid residues (i.e. the full length of SEQ ID NO:6) when compared to SEQ ID NO:6 using DNAsiS™ as described above.

D. Additional sequence corresponding to the 3' end of nDiADC$_{456}$ was obtained as follows. A first PCR amplification was carried out using primers with SEQ ID NO:2 and SEQ ID NO:4 and "touchdown" PCR as described in section B. The product of this first PCR reaction was used as the template for a second PCR reaction using forward primer DIADC1F, having the nucleotide sequence 5' GCT GGA TTG GCT TGG TCG AAT GAT TGG 3', represented by SEQ ID NO:8 and corresponding to nucleotides 241–264 of nDiADC$_{456}$, and the reverse primer with SEQ ID NO:4.

The resulting product, denoted nDiADC$_{475}$, was approximately 475-bp when visualized on an agarose gel. The PCR product was subcloned into the pCRII TA™ vector, available from Invitrogen, according to the manufacturer's instructions and subjected to DNA sequence analysis using standard techniques. The nucleic acid sequence of the coding strand of nDiADC$_{475}$ is denoted herein as SEQ ID NO:9 and its complementary sequence is denoted herein as SEQ ID NO:11. Translation of SEQ ID NO:9 yields a protein of about 158 amino acids, denoted herein as PDiADC$_{158}$, the amino acid sequence of which is presented in SEQ ID NO:10, assuming a first in-frame codon extending from nucleotide 1 to nucleotide 3 of SEQ ID NO:9.

Homology searches were performed on SEQ ID NO:9 and SEQ ID NO:10, using the blastn and blastp programs, respectively, available through the BLAST network of the NCBI. The highest scoring match of the homology search at the nucleotide level was *C. elegans* putative ADC-like nucleic acid molecule, EMBL Accession No. Z49068. The 1770-bp, computer predicted *C. elegans* cDNA sequence described above was compared to SEQ ID NO:9 using the DNAsis™ computer program as described above which revealed 68.4% identity over 475 nucleotides (i.e. the full length of SEQ ID NO:9). The highest scoring match at the amino acid level was *C. elegans* putative ADC-like protein, EMBL Accession No. 780197 with 81.6% identity over 158 amino acid residues (i.e. the full length of SEQ ID NO:10) when compared to SEQ ID NO:10 using DNAsis™ as described in section C.

E. Additional sequence corresponding to the 5' end of nDiADC$_{456}$ was obtained as follows. A first PCR amplification was carried out with primers with SEQ ID NO:2 and SEQ ID NO:4 and "touchdown" PCR described in section B. The product of this first PCR reaction was used as the template for a second PCR reaction using reverse primer DIADC2R, having the nucleotide sequence 5' CTG AGA GGA CGT CAA AGG AGC AGC AGG 3', represented by SEQ ID NO:12, and corresponding to nucleotides 398–424 of nDiADC$_{456}$, and forward primer with SEQ ID NO:2. The resulting product, denoted nDiADC$_{517}$, was approximately 517 bp when visualized on an agarose gel. The PCR product was subcloned into the pCRII TA™ vector, available from Invitrogen, according to the manufacturer's instructions and subjected to DNA sequence analysis using standard techniques. The nucleic acid sequence of the coding strand of nDiADC$_{517}$ is denoted herein as SEQ ID NO:13 and its complementary sequence is denoted herein as SEQ ID NO:15. Translation of SEQ ID NO:13 yields a protein of about 172 amino acids, denoted herein as PDiADC$_{172}$, the amino acid sequence of which is presented in SEQ ID NO:14, assuming a first in-frame codon extending from nucleotide 1 to nucleotide 3 of SEQ ID NO:13.

Homology searches were performed on SEQ ID NO:13 and SEQ ID NO:14, using the blastn and blastp programs, respectively, available through the BLAST network of the NCBI. The highest scoring match of the homology search at the nucleotide level was *C. elegans* putative ADC-like nucleic acid molecule EMBL Accession No. Z49068. The 1770-bp, computer predicted *C. elegans* cDNA sequence described above was compared to SEQ ID NO:13 using the DNAsis™ computer program as described in section C which revealed 66.5% identity over 517 nucleotides (i.e. the full length of SEQ ID NO:13). The highest scoring match at the amino acid level was *C. elegans* putative ADC-like protein EMBL Accession No. 780197 with 86.0% identity over 172 amino acid residues (i.e. the full length of SEQ ID NO:14) when compared to SEQ ID NO:14 using DNAsis™ as described in section C.

F. The nucleic acid sequences of nDiADC$_{456}$, nDiADC$_{475}$ and nDiADC$_{517}$ were aligned and a contiguous nucleic acid sequence was derived. The resulting contiguous sequence, denoted nDiADC$_{808}$, was 808-bp in length. The nucleic acid sequence of the coding strand of nDiADC$_{808}$ is denoted herein as SEQ ID NO:16 and its complement is denoted herein as SEQ ID NO:18. Translation of SEQ ID NO:16 suggests that nucleic acid molecule nDiADC$_{808}$ encodes a non-full-length *D. immitis* ADC protein of about 269 amino acids, referred to herein as PDiADC$_{269}$, having amino acid sequence SEQ ID NO:17, assuming the first codon spans from nucleotide 1 through nucleotide 3 of SEQ ID NO 16.

Homology searches were performed on SEQ ID NO:16 and SEQ ID NO:17, using the blastn and blastp programs, respectively, available through the BLAST network of the NCBI. The highest scoring match of the homology search at the nucleotide level was *C. elegans* putative ADC-like nucleic acid molecule EMBL Accession No. Z49068. The 1770-bp, computer predicted *C. elegans* cDNA sequence described above was compared to SEQ ID NO:16 using the DNAsis™ computer program as described in section C, which revealed 64.9% identity over 808 nucleotides (i.e. the full length of SEQ ID NO:16). The highest scoring match at the amino acid level was *C. elegans* putative ADC-like protein EMBL Accession No. 780197 with 82.5% identity over 269 amino acid residues (i.e. the full length of SEQ ID NO:17) when compared to SEQ ID NO:17 using DNAsis™ as described in section C.

Example 6

This example describes the identification and sequencing of a nucleic acid molecule encoding a *Brugia malayi* aromatic amino acid decarboxylase protein.

A *Brugia malayi* ADC nucleic acid molecule of about 549-bp was isolated from adult *B. malayi* first strand cDNA (reverse transcribed from adult *B. malayi* mRNA) by PCR amplification as follows. Adult *B. malayi* first-strand cDNA was used as the template in a first PCR amplification with primers with SEQ ID NO:2 and SEQ ID NO:4 using the modified "touchdown" PCR protocol described in Example 5. The product of the first PCR reaction was used as the template in a second PCR amplification using primers SEQ ID NO:2 and SEQ ID NO:3. A 549-bp DNA fragment, denoted herein as nBmADC$_{549}$, was isolated from the PCR product by agarose gel electrophoresis and was shown to hybridize to nDiADC$_{456}$ by Southern hybridization under low stringency conditions (0.1 SSC, 0.1% SDS at 42 C.). The PCR-amplified fragment containing nBmADC$_{549}$ was excised from the gel and purified using a QIAquick™ kit, available from Qiagen, according to the manufacturer's instructions. The resultant 549-bp DNA fragment was subcloned into the pCRII TA™ vector, available from Invitrogen, according to the manufacturer's instructions.

The nucleic acid molecule nBmADC$_{549}$ was sequenced by the Sanger dideoxy chain as described in Example 5. The resulting nucleic acid sequence of nBmADC$_{549}$ has a coding strand presented herein as SEQ ID NO:19 and a complementary strand presented herein as SEQ ID NO:21.

Translation of SEQ ID NO:19 yields a protein of about 183 amino acids, denoted herein as PDiADC$_{183}$, the amino acid sequence of which is presented in SEQ ID NO:20, assuming a first in-frame codon extending from nucleotide 1 to nucleotide 3 of SEQ ID NO:19.

Homology searches were performed on SEQ ID NO:19 and SEQ ID NO:20, using the blastn and blastp programs, respectively, available through the BLAST network of the NCBI. The highest scoring match of the homology search at the nucleotide level was to *C. elegans* putative ADC-like nucleic acid molecule EMBL Accession No. Z49068. The 1770-bp, computer predicted *C. elegans* cDNA sequence described in Example 5 was compared to SEQ ID NO:19 using the DNAsis™ computer program which revealed 65.2% identity over 549 nucleotides (i.e. the full length of SEQ ID NO:19). The highest scoring match at the amino acid level was to *C. elegans* putative ADC-like protein EMBL Accession No. 780197, with 85.7% identity over 183 amino acid residues (i.e. the full length of SEQ ID NO:20) when compared to SEQ ID NO:20 using DNAsis™ as described in Example 5.

A comparison was also done between nBmADC$_{549}$ (SEQ ID NO:19) and nDiADC$_{808}$ (SEQ ID NO:16) and their corresponding proteins using DNAsis™ as described in Example 5. At the nucleotide level, these molecules shared 88.3% identity over 549 nucleotides (i.e. the full length of SEQ ID NO:19) and at the amino acid level they shared 96.7% identity over 183 amino acid residues (i.e. the full length of SEQ ID NO:20).

Example 7

This Example describes the effect of a number of protease inhibitors on *D. immitis* larval viability in a larval culture system.

The following enzyme inhibitors were tested in the culture system described below at the indicated final concentrations:

(a) Pefabloc, at concentrations of 0.004, 0.04 and 0.4 mM;
(b) PMSF, at concentrations of 0.01, 0.1 and 1 mM;
(c) 3,4 DCI, at concentrations of 0.001, 0.01 and 0.1 mM
(d) APMSF, at concentrations of 0.001, 0.01 and 0.1 mM The general protocol for the larval viability assays was as follows: Twenty-five *D. immitis* L3 larvae were cultured for 3 days in 1 ml of NI media containing antibiotics and 20% SeruMax, available from Sigma Chemical. Inhibitors were added to each culture on day 1 and the cultures were examined microscopically every 24 hours until day 3, when the cultures were terminated. The number of larvae that molted were determined by counting shed cuticles. Each inhibitor and concentration was repeated 3 times for a total of 75 larvae tested at each concentration and the results pooled to determine percent inhibition. These results are summarized in Table IV.

TABLE IV

Inhibition of molting of L3 larvae by protease inhibitors

| Inhibitors | Concentration(mM) | % Inhibition |
|---|---|---|
| Pefabloc | 0.4 | 100% |
|  | 0.04 | 44.6% |
|  | 0.004 | 23.5% |
| PMSF | 1 | 47.3% |
|  | 0.1 | 29.8% |
|  | 0.01 | 32.3% |
| 3,4 DCI | 0.1 | 100% |
|  | 0.01 | 40.9% |
|  | 0.001 | 28.6% |
| APMSF | 0.1 | 19.7% |
|  | 0.01 | 24.2% |
|  | 0.001 | 14.1% |

These results indicate that Pefabloc at a final concentration of 0.4 mM and 3,4 DCI at a final concentration of 0.1 mM, completely inhibited the molting process whereas PMSF and APMSF were unable to completely inhibit the molting of L3 to L4 at the highest concentrations used. These results indicate that there is a good correlation between the ability of the inhibitors to inhibit molting and the inhibition of Di-ADC activity.

The effect of Pefabloc on the development of *D. immitis* L3 larvae was investigated by adding the inhibitor into the culture at different times. Pefabloc was added to larval cultures at a final concentration of 0.3 mM at various time points during culture, listed in Table V below, and the effect on molting was measured as described herein. The results shown in Table V indicate that the effect of Pefabloc on *D. immitis* larvae is to inhibit molting during early development. Adding the inhibitor into the culture at day 1 or day 2 inhibited the molt completely whereas inhibitor added on day 3 had no apparent effect on molting.

TABLE V

Effect of Pefabloc (0.3 mM) on L3 molting at different time points. Asterisks indicates experiments with duplicate trials.

| Pefabloc | L3 (n) | Molted L3 (n) | Molted (%) |
|---|---|---|---|
| No Pefabloc | 32 | 22 | 68.8 |
| Day 1–Day 3 | 30 | 0 | 0 |
| Day 1 and Day 3 | 32, 33* | 0 | 0 |

TABLE V-continued

Effect of Pefabloc (0.3 mM) on L3 molting at different time points. Asterisks indicates experiments with duplicate trials.

| Pefabloc | L3 (n) | Molted L3 (n) | Molted (%) |
|---|---|---|---|
| Day 2–Day 3 | 28, 29* | 0 | 0 |
| Day 3 | 28, 30* | 18, 22* | 68.7 |

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method for detecting the presence of an amino acid decarboxylase, said method comprising the steps of: (a) contacting a putative amino acid decarboxylase-containing composition with a synthetic substrate to create a reaction product. wherein said synthetic substrate comprises phenylalanine conjugated to a tag which produces a reference signal, wherein said tag is cleaved from said synthetic substrate in the presence of an amino acid decarboxylase resulting in a cleavage product which produces a cleavage signal which is different from said reference signal; and (b) observing a reaction signal produced by said reaction product and comparing said reaction signal with said reference signal and said cleavage signal, wherein a reaction signal equivalent to said cleavage signal indicates the presence of an amino acid decarboxylase.

2. The method of claim 1 further comprising the step of comparing the intensity of said reaction signal to said cleavage signal, wherein the intensity of said cleavage signal indicates the amount of an amino acid decarboxylase present in said sample.

3. The method of claim 2, wherein said synthetic substrate comprises a compound having the formula:

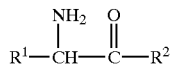

wherein R¹ represents phenylalanine; and wherein R² represents a tag selected from the group consisting of a fluorescent tag and a colorimetric tag.

4. The method of claim 3, wherein said tag is selected from the group consisting of: 7-amido-4-methylcoumarin, 4-methylcoumarin, 2-naphthylamine, 4-methoxy-2-naphthylamine, o-phthalaldehyde, cresyl violet, 5-nitrosalicylaldehyde, 7-hydroxy-4-trifluoromethylcoumarin, rhodamine 110, naphthyl AS-MX, 7-amino-4-trifluoromethylquinolone, naphthyl AS-TR, 5,5'-dithio-bis-2-nitrobenzoic acid, 6-amino-2-quinolone, 6-amino-2-styrylquinoline, 4-nitroanilide, 5-aminoisopohthalic acid dimethyl Esther, 4-methylumbelliferone, and naphthyl AS-BI.

5. A method for detecting the presence of an amino acid decarboxylase, said method comprising the steps of: (a) contacting a putative amino acid decarboxylase-containing composition with a synthetic substrate to create a reaction product, wherein said synthetic substrate comprises phenylalanine conjugated to a tag which produces a reference signal, wherein said tag is cleaved from said synthetic substrate in the presence of an amino acid decarboxylase resulting in a cleavage product which produces a cleavage signal which is different from said reference signal; and (b) observing said reaction product or a reaction signal produced by said reaction product and comparing said reaction product or reaction signal with said cleavage product, said cleavage signal and said reference signal; wherein a reaction product about the same size as said cleavage product, a reaction signal about the same emission wavelength as said cleavage signal or a reaction signal about the same color as said cleavage signal indicates the presence of an amino acid decarboxylase.

6. The method of claim 5, wherein said synthetic substrate comprises a compound having the formula:

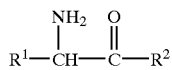

wherein R¹ represents phenylalanine; and wherein R² represents a tag selected from the group consisting of a fluorescent tag and a colorimetric tag.

7. The method of claim 5, wherein said tag is selected from the group consisting of: 7-amido-4-methylcoumarin, 4-methylcoumarin, 2-naphthylamine, 4-methoxy-2-naphthylamine, o-phthalaldehyde, cresyl violet, 5-nitrosalicylaldehyde, 7-hydroxy-4-trifluoromethylcoumarin, rhodamine 110, naphthyl AS-MX, 7-amino-4-trifluoromethylquinolone, naphthyl AS-TR, 5,5'-dithio-bis-2-nitrobenzoic acid, 6-amino-2-quinolone, 6-amino-2-styrylquinoline, 4-nitroanilide, 5-aminoisopohthalic acid dimethyl Esther, 4-methylumbelliferone, and naphthyl AS-BI.

* * * * *

SEQUENCE LISTING

<160> NUMBER OF SEQ ID NOS: 22

<210> SEQ ID NO 1
<211> LENGTH: 20
<212> TYPE: PRT
<213> ORGANISM: Dirofilaria immitis

<400> SEQUENCE: 1

Gln Leu Tyr Ile Lys Gln Val Gln Val Gln Lys Arg Gln Glu Lys Ile
1               5                   10                  15

Glu Tyr Gln Val
            20

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer
<223> OTHER INFORMATION: At locations 9, 18, 21 and 24, n = a or g or c or
      t

<400> SEQUENCE: 2
ttycaygcnt ayttyccngc nggnaay                                          27

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer
<223> OTHER INFORMATION: At locations 4, 7, 13 and 19, n = a or g or c or t

<400> SEQUENCE: 3
rtangcngcr tcnacrtgna rcca                                             24

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence:  Synthetic
      Primer
<223> OTHER INFORMATION: At locations 9, 15, 18, 21, 27 and 30, n = a or g -continued

```
                or c or t

<400> SEQUENCE: 4
acraaccana ryttnarncw nckraanckn c                                    31

<210> SEQ ID NO 5
<211> LENGTH: 456
<212> TYPE: DNA
<213> ORGANISM: Dirofilaria immitis
<220> FEATURE:
<221> NAME/KEY: CDS
<222> LOCATION: (1)..(456)

<400> SEQUENCE: 5 ata att atg ctg gat tgg ctt ggt cga atg att ggt ctt cca gat gct        48
Ile Ile Met Leu Asp Trp Leu Gly Arg Met Ile Gly Leu Pro Asp Ala
 1               5                  10                  15 ttt ttg cca ttc acc gaa aat gga aaa ggt ggc ggt gtt att cag ggt        96
Phe Leu Pro Phe Thr Glu Asn Gly Lys Gly Gly Gly Val Ile Gln Gly
             20                  25                  30 tct gca agt gaa tgt aat ttt gtt tcg cta tta gca gca cga ttt gaa       144
Ser Ala Ser Glu Cys Asn Phe Val Ser Leu Leu Ala Ala Arg Phe Glu
         35                  40                  45 gtg ctc aaa gag ctt aaa caa cgt ttt cca ttt gtt gaa gaa gga cta       192
Val Leu Lys Glu Leu Lys Gln Arg Phe Pro Phe Val Glu Glu Gly Leu
     50                  55                  60 ttg ctg tca aaa tta gtc gca tat tgt tct aaa gaa gct cat tca tca       240
Leu Leu Ser Lys Leu Val Ala Tyr Cys Ser Lys Glu Ala His Ser Ser
 65                  70                  75                  80 gtc gag aag gct tgc atg atc ggc atg gtt aaa ttg aag att ttg gac       288
Val Glu Lys Ala Cys Met Ile Gly Met Val Lys Leu Lys Ile Leu Asp
                 85                  90                  95 act gat gca aag ttt cgt tta cgt ggt gaa aca tta cgt ctg gca ata       336
Thr Asp Ala Lys Phe Arg Leu Arg Gly Glu Thr Leu Arg Leu Ala Ile
            100                 105                 110 gag gaa gat cgt aat ctt ggc tta ata ccg ttt ttt gtt tcc act act       384
Glu Glu Asp Arg Asn Leu Gly Leu Ile Pro Phe Phe Val Ser Thr Thr
        115                 120                 125 ctt ggc acc aca tcc tgc tgc tcc ttt gac gtc ctc tca gaa att gga       432
Leu Gly Thr Thr Ser Cys Cys Ser Phe Asp Val Leu Ser Glu Ile Gly
    130                 135                 140 ccc gtt tgt caa gaa aat gat tta                                       456
Pro Val Cys Gln Glu Asn Asp Leu
145                 150

<210> SEQ ID NO 6
<211> LENGTH: 152
<212> TYPE: PRT
<213> ORGANISM: Dirofilaria immitis

<400> SEQUENCE: 6

Ile Ile Met Leu Asp Trp Leu Gly Arg Met Ile Gly Leu Pro Asp Ala
 1               5                  10                  15

Phe Leu Pro Phe Thr Glu Asn Gly Lys Gly Gly Gly Val Ile Gln Gly
             20                  25                  30

Ser Ala Ser Glu Cys Asn Phe Val Ser Leu Leu Ala Ala Arg Phe Glu
         35                  40                  45

Val Leu Lys Glu Leu Lys Gln Arg Phe Pro Phe Val Glu Glu Gly Leu
     50                  55                  60

Leu Leu Ser Lys Leu Val Ala Tyr Cys Ser Lys Glu Ala His Ser Ser
 65                  70                  75                  80
```

```
Val Glu Lys Ala Cys Met Ile Gly Met Val Lys Leu Lys Ile Leu Asp
                85                  90                  95

Thr Asp Ala Lys Phe Arg Leu Arg Gly Glu Thr Leu Arg Leu Ala Ile
            100                 105                 110

Glu Glu Asp Arg Asn Leu Gly Leu Ile Pro Phe Phe Val Ser Thr Thr
        115                 120                 125

Leu Gly Thr Thr Ser Cys Cys Ser Phe Asp Val Leu Ser Glu Ile Gly
    130                 135                 140

Pro Val Cys Gln Glu Asn Asp Leu
145                 150

<210> SEQ ID NO 7
<211> LENGTH: 456
<212> TYPE: DNA
<213> ORGANISM: Dirofilaria immitis

<400> SEQUENCE: 7
taaatcattt tcttgacaaa cgggtccaat ttctgagagg acgtcaaagg agcagcagga    60
tgtggtgcca agagtagtgg aaacaaaaaa cggtattaag ccaagattac gatcttcctc   120
tattgccaga cgtaatgttt caccacgtaa acgaaacttt gcatcagtgt ccaaaatctt   180
caatttaacc atgccgatca tgcaagcctt ctcgactgat gaatgagctt ctttagaaca   240
atatgcgact aattttgaca gcaatagtcc ttcttcaaca aatggaaaac gttgtttaag   300
ctctttgagc acttcaaatc gtgctgctaa tagcgaaaca aaattacatt cacttgcaga   360
accctgaata acaccgccac cttttccatt tcggtgaat ggcaaaaaag catctggaag    420
accaatcatt cgaccaagcc aatccagcat aattat                             456

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
gctggattgg cttggtcgaa tgattgg                                        27

<210> SEQ ID NO 9
<211> LENGTH: 475
<212> TYPE: DNA
<213> ORGANISM: Dirofilaria immitis
<220> FEATURE:
<221> NAME/KEY: CDS
<222> LOCATION: (1)..(474)

<400> SEQUENCE: 9 gtc gag aag gct tgc atg atc ggc atg gtt aaa ttg aag att ttg gac     48
Val Glu Lys Ala Cys Met Ile Gly Met Val Lys Leu Lys Ile Leu Asp
  1               5                  10                  15 act gat gca aag ttt cgt tta cgt ggt gaa aca tta cgt ctg gca ata     96
Thr Asp Ala Lys Phe Arg Leu Arg Gly Glu Thr Leu Arg Leu Ala Ile
             20                  25                  30 gag gaa gat cgt aat ctt ggc tta ata ccg ttt ttt gtt tcc act act    144
Glu Glu Asp Arg Asn Leu Gly Leu Ile Pro Phe Phe Val Ser Thr Thr
         35                  40                  45 ctt ggc acc aca tcc tgc tgc tcc ttt gac gtc ctc tca gaa att gga   192
Leu Gly Thr Thr Ser Cys Cys Ser Phe Asp Val Leu Ser Glu Ile Gly
     50                  55                  60
```

```
ccc gtt tgt caa gaa aat gat tta tgg cta cat gta gat gga gcg tat    240
Pro Val Cys Gln Glu Asn Asp Leu Trp Leu His Val Asp Gly Ala Tyr
 65                  70                  75                  80 gga gga agt gcg atg att tgc cca gaa ttc cga ccg cta atg gaa ggg    288
Gly Gly Ser Ala Met Ile Cys Pro Glu Phe Arg Pro Leu Met Glu Gly
                 85                  90                  95 atc gaa tgt gcg atg agt ttc aac acc aat cca aat aaa ttc atg ctc    336
Ile Glu Cys Ala Met Ser Phe Asn Thr Asn Pro Asn Lys Phe Met Leu
100                 105                 110 gtc aat ttt gat tgt tct aca atg tgg gta aaa gat cgc tac aag cta    384
Val Asn Phe Asp Cys Ser Thr Met Trp Val Lys Asp Arg Tyr Lys Leu
        115                 120                 125 acc caa gct cta gtt gtt gat cct cta tac ttg caa cac agt tgg aca    432
Thr Gln Ala Leu Val Val Asp Pro Leu Tyr Leu Gln His Ser Trp Thr
    130                 135                 140 gac aag gca ata gat tat cgt cat tgg agt ata cca ctt agt c          475
Asp Lys Ala Ile Asp Tyr Arg His Trp Ser Ile Pro Leu Ser
145                 150                 155

<210> SEQ ID NO 10
<211> LENGTH: 158
<212> TYPE: PRT
<213> ORGANISM: Dirofilaria immitis

<400> SEQUENCE: 10

Val Glu Lys Ala Cys Met Ile Gly Met Val Lys Leu Lys Ile Leu Asp
  1               5                  10                  15

Thr Asp Ala Lys Phe Arg Leu Arg Gly Glu Thr Leu Arg Leu Ala Ile
             20                  25                  30

Glu Glu Asp Arg Asn Leu Gly Leu Ile Pro Phe Phe Val Ser Thr Thr
         35                  40                  45

Leu Gly Thr Thr Ser Cys Cys Ser Phe Asp Val Leu Ser Glu Ile Gly
     50                  55                  60

Pro Val Cys Gln Glu Asn Asp Leu Trp Leu His Val Asp Gly Ala Tyr
 65                  70                  75                  80

Gly Gly Ser Ala Met Ile Cys Pro Glu Phe Arg Pro Leu Met Glu Gly
                 85                  90                  95

Ile Glu Cys Ala Met Ser Phe Asn Thr Asn Pro Asn Lys Phe Met Leu
            100                 105                 110

Val Asn Phe Asp Cys Ser Thr Met Trp Val Lys Asp Arg Tyr Lys Leu
        115                 120                 125

Thr Gln Ala Leu Val Val Asp Pro Leu Tyr Leu Gln His Ser Trp Thr
    130                 135                 140

Asp Lys Ala Ile Asp Tyr Arg His Trp Ser Ile Pro Leu Ser
145                 150                 155

<210> SEQ ID NO 11
<211> LENGTH: 475
<212> TYPE: DNA
<213> ORGANISM: Dirofilaria immitis

<400> SEQUENCE: 11
gactaagtgg tatactccaa tgacgataat ctattgcctt gtctgtccaa ctgtgttgca    60
agtatagagg atcaacaact agagcttggg ttagcttgta gcgatctttt acccacattg   120
tagaacaatc aaaattgacg agcatgaatt tatttggatt ggtgttgaaa ctcatcgcac   180
attcgatccc ttccattagc ggtcggaatt ctgggcaaat catcgcactt cctccatacg   240
```

```
ctccatctac atgtagccat aaatcatttt cttgacaaac gggtccaatt tctgagagga    300
cgtcaaagga gcagcaggat gtggtgccaa gagtagtgga acaaaaaac  ggtattaagc    360 caagattacg atcttcctct attgccagac gtaatgtttc accacgtaaa cgaaactttg    420
catcagtgtc caaaatcttc aatttaacca tgccgatcat gcaagccttc tcgac         475
```

```
<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
ctgagaggac gtcaaaggag cagcagg                                         27

<210> SEQ ID NO 13
<211> LENGTH: 517
<212> TYPE: DNA
<213> ORGANISM: Dirofilaria immitis
<220> FEATURE:
<221> NAME/KEY: CDS
<222> LOCATION: (1)..(516)

<400> SEQUENCE: 13
```

| gct | ttt | ccg | aat | att | ttg | gct | gat | atg | att | tca | gat | gct | att | ggt | gca |  48 |
| Ala | Phe | Pro | Asn | Ile | Leu | Ala | Asp | Met | Ile | Ser | Asp | Ala | Ile | Gly | Ala |     |
|  1  |     |     |     |  5  |     |     |     |     | 10  |     |     |     |     | 15  |     |     |

| gtt | ggc | ttt | tct | tgg | gcc | gca | tgt | cct | gca | atg | act | gaa | tta | gaa | ata |  96 |
| Val | Gly | Phe | Ser | Trp | Ala | Ala | Cys | Pro | Ala | Met | Thr | Glu | Leu | Glu | Ile |     |
|     |     |     |  20 |     |     |     |     |  25 |     |     |     |     |  30 |     |     |     |

| att | atg | ctg | gat | tgg | ctt | ggt | cga | atg | att | ggc | ctt | cca | gat | gct | ttt | 144 |
| Ile | Met | Leu | Asp | Trp | Leu | Gly | Arg | Met | Ile | Gly | Leu | Pro | Asp | Ala | Phe |     |
|     |     |  35 |     |     |     |     |  40 |     |     |     |     |  45 |     |     |     |     |

| ttg | cca | ttc | acc | gaa | aat | gga | aaa | ggt | ggc | ggt | gtt | att | cag | ggt | tct | 192 |
| Leu | Pro | Phe | Thr | Glu | Asn | Gly | Lys | Gly | Gly | Gly | Val | Ile | Gln | Gly | Ser |     |
|  50 |     |     |     |     |  55 |     |     |     |     |  60 |     |     |     |     |     |     |

| gca | agt | gaa | tgt | aat | ttt | gtt | tcg | cta | tta | gca | gca | cga | ttt | gaa | gtg | 240 |
| Ala | Ser | Glu | Cys | Asn | Phe | Val | Ser | Leu | Leu | Ala | Ala | Arg | Phe | Glu | Val |     |
|  65 |     |     |     |     |  70 |     |     |     |     |  75 |     |     |     |     |  80 |     |

| ctc | aaa | gag | ctt | aaa | caa | cgt | ttt | cca | ttt | gtt | gaa | gaa | gga | cta | ttg | 288 |
| Leu | Lys | Glu | Leu | Lys | Gln | Arg | Phe | Pro | Phe | Val | Glu | Glu | Gly | Leu | Leu |     |
|     |     |     |     |  85 |     |     |     |     |  90 |     |     |     |     |  95 |     |     |

| ctg | tca | aaa | tta | gtc | gca | tat | tgt | tct | aaa | gaa | gct | cat | tca | tca | gtc | 336 |
| Leu | Ser | Lys | Leu | Val | Ala | Tyr | Cys | Ser | Lys | Glu | Ala | His | Ser | Ser | Val |     |
|     |     |     | 100 |     |     |     |     | 105 |     |     |     |     | 110 |     |     |     |

| gag | aag | gct | tgc | atg | atc | ggc | atg | gtt | aaa | ttg | aag | att | ttg | gac | act | 384 |
| Glu | Lys | Ala | Cys | Met | Ile | Gly | Met | Val | Lys | Leu | Lys | Ile | Leu | Asp | Thr |     |
|     |     | 115 |     |     |     |     | 120 |     |     |     |     | 125 |     |     |     |     |

| gat | gca | aag | ttt | cgt | tta | cgt | ggt | gaa | aca | tta | cgt | ctg | gca | ata | gag | 432 |
| Asp | Ala | Lys | Phe | Arg | Leu | Arg | Gly | Glu | Thr | Leu | Arg | Leu | Ala | Ile | Glu |     |
|     | 130 |     |     |     |     | 135 |     |     |     |     | 140 |     |     |     |     |     |

| gaa | gat | cgt | aat | ctt | ggc | tta | ata | ccg | ttt | ttt | gtt | tcc | act | act | ctt | 480 |
| Glu | Asp | Arg | Asn | Leu | Gly | Leu | Ile | Pro | Phe | Phe | Val | Ser | Thr | Thr | Leu |     |
| 145 |     |     |     |     | 150 |     |     |     |     | 155 |     |     |     |     | 160 |     |

| ggc | acc | aca | tcc | tgc | tgc | tcc | ttt | gac | gtc | ctc | tca | g   |     |     |     | 517 |
| Gly | Thr | Thr | Ser | Cys | Cys | Ser | Phe | Asp | Val | Leu | Ser |     |     |     |     |     |
|     |     |     |     | 165 |     |     |     |     | 170 |     |     |     |     |     |     |     |

```
<210> SEQ ID NO 14
<211> LENGTH: 172
```

-continued

<212> TYPE: PRT
<213> ORGANISM: Dirofilaria immitis

<400> SEQUENCE: 14

```
Ala Phe Pro Asn Ile Leu Ala Asp Met Ile Ser Asp Ala Ile Gly Ala
  1               5                  10                  15

Val Gly Phe Ser Trp Ala Ala Cys Pro Ala Met Thr Glu Leu Glu Ile
             20                  25                  30

Ile Met Leu Asp Trp Leu Gly Arg Met Ile Gly Leu Pro Asp Ala Phe
         35                  40                  45

Leu Pro Phe Thr Glu Asn Gly Lys Gly Gly Gly Val Ile Gln Gly Ser
     50                  55                  60

Ala Ser Glu Cys Asn Phe Val Ser Leu Leu Ala Ala Arg Phe Glu Val
 65                  70                  75                  80

Leu Lys Glu Leu Lys Gln Arg Phe Pro Phe Val Glu Glu Gly Leu Leu
                 85                  90                  95

Leu Ser Lys Leu Val Ala Tyr Cys Ser Lys Glu Ala His Ser Ser Val
            100                 105                 110

Glu Lys Ala Cys Met Ile Gly Met Val Lys Leu Lys Ile Leu Asp Thr
        115                 120                 125

Asp Ala Lys Phe Arg Leu Arg Gly Glu Thr Leu Arg Leu Ala Ile Glu
    130                 135                 140

Glu Asp Arg Asn Leu Gly Leu Ile Pro Phe Phe Val Ser Thr Thr Leu
145                 150                 155                 160

Gly Thr Thr Ser Cys Cys Ser Phe Asp Val Leu Ser
                165                 170
```

<210> SEQ ID NO 15
<211> LENGTH: 517
<212> TYPE: DNA
<213> ORGANISM: Dirofilaria immitis

<400> SEQUENCE: 15

```
ctgagaggac gtcaaaggag cagcaggatg tggtgccaag agtagtggaa acaaaaaacg  60
gtattaagcc aagattacga tcttcctcta ttgccagacg taatgtttca ccacgtaaac 120
gaaactttgc atcagtgtcc aaaatcttca atttaaccat gccgatcatg caagccttct 180
cgactgatga atgagcttct ttagaacaat atgcgactaa ttttgacagc aatagtcctt 240
cttcaacaaa tggaaaacgt tgtttaagct ctttgagcac ttcaaatcgt gctgctaata 300
gcgaaacaaa attacattca cttgcagaac cctgaataac accgccacct tttccatttt 360
cggtgaatgg caaaaaagca tctggaaggc caatcattcg accaagccaa tccagcataa 420
ttatttctaa ttcagtcatt gcaggacatg cggcccaaga aaagccaact gcaccaatag 480
catctgaaat catatcagcc aaaatattcg gaaaagc                          517
```

<210> SEQ ID NO 16
<211> LENGTH: 808
<212> TYPE: DNA
<213> ORGANISM: Dirofilaria immitis
<220> FEATURE:
<221> NAME/KEY: CDS
<222> LOCATION: (1)..(807)

<400> SEQUENCE: 16

```
gct ttt ccg aat att ttg gct gat atg att tca gat gct att ggt gca    48
Ala Phe Pro Asn Ile Leu Ala Asp Met Ile Ser Asp Ala Ile Gly Ala
  1               5                  10                  15
```

-continued

```
gtt ggc ttt tct tgg gcc gca tgt cct gca atg act gaa tta gaa ata     96
Val Gly Phe Ser Trp Ala Ala Cys Pro Ala Met Thr Glu Leu Glu Ile
         20                  25                  30 att atg ctg gat tgg ctt ggt cga atg att ggc ctt cca gat gct ttt    144
Ile Met Leu Asp Trp Leu Gly Arg Met Ile Gly Leu Pro Asp Ala Phe
     35                  40                  45 ttg cca ttc acc gaa aat gga aaa ggt ggc ggt gtt att cag ggt tct    192
Leu Pro Phe Thr Glu Asn Gly Lys Gly Gly Gly Val Ile Gln Gly Ser
 50                  55                  60 gca agt gaa tgt aat ttt gtt tcg cta tta gca gca cga ttt gaa gtg    240
Ala Ser Glu Cys Asn Phe Val Ser Leu Leu Ala Ala Arg Phe Glu Val
 65                  70                  75                  80 ctc aaa gag ctt aaa caa cgt ttt cca ttt gtt gaa gaa gga cta ttg    288
Leu Lys Glu Leu Lys Gln Arg Phe Pro Phe Val Glu Glu Gly Leu Leu
             85                  90                  95 ctg tca aaa tta gtc gca tat tgt tct aaa gaa gct cat tca tca gtc    336
Leu Ser Lys Leu Val Ala Tyr Cys Ser Lys Glu Ala His Ser Ser Val
        100                 105                 110 gag aag gct tgc atg atc ggc atg gtt aaa ttg aag att ttg gac act    384
Glu Lys Ala Cys Met Ile Gly Met Val Lys Leu Lys Ile Leu Asp Thr
    115                 120                 125 gat gca aag ttt cgt tta cgt ggt gaa aca tta cgt ctg gca ata gag    432
Asp Ala Lys Phe Arg Leu Arg Gly Glu Thr Leu Arg Leu Ala Ile Glu
130                 135                 140 gaa gat cgt aat ctt ggc tta ata ccg ttt ttt gtt tcc act act ctt    480
Glu Asp Arg Asn Leu Gly Leu Ile Pro Phe Phe Val Ser Thr Thr Leu
145                 150                 155                 160 ggc acc aca tcc tgc tgc tcc ttt gac gtc ctc tca gaa att gga ccc    528
Gly Thr Thr Ser Cys Cys Ser Phe Asp Val Leu Ser Glu Ile Gly Pro
                165                 170                 175 gtt tgt caa gaa aat gat tta tgg cta cat gta gat gga gcg tat gga    576
Val Cys Gln Glu Asn Asp Leu Trp Leu His Val Asp Gly Ala Tyr Gly
            180                 185                 190 gga agt gcg atg att tgc cca gaa ttc cga ccg cta atg gaa ggg atc    624
Gly Ser Ala Met Ile Cys Pro Glu Phe Arg Pro Leu Met Glu Gly Ile
        195                 200                 205 gaa tgt gcg atg agt ttc aac acc aat cca aat aaa ttc atg ctc gtc    672
Glu Cys Ala Met Ser Phe Asn Thr Asn Pro Asn Lys Phe Met Leu Val
    210                 215                 220 aat ttt gat tgt tct aca atg tgg gta aaa gat cgc tac aag cta acc    720
Asn Phe Asp Cys Ser Thr Met Trp Val Lys Asp Arg Tyr Lys Leu Thr
225                 230                 235                 240 caa gct cta gtt gtt gat cct cta tac ttg caa cac agt tgg aca gac    768
Gln Ala Leu Val Val Asp Pro Leu Tyr Leu Gln His Ser Trp Thr Asp
                245                 250                 255 aag gca ata gat tat cgt cat tgg agt ata cca ctt agt c              808
Lys Ala Ile Asp Tyr Arg His Trp Ser Ile Pro Leu Ser
            260                 265
```

<210> SEQ ID NO 17
<211> LENGTH: 269
<212> TYPE: PRT
<213> ORGANISM: Dirofilaria immitis

<400> SEQUENCE: 17

```
Ala Phe Pro Asn Ile Leu Ala Asp Met Ile Ser Asp Ala Ile Gly Ala
 1               5                  10                  15

Val Gly Phe Ser Trp Ala Ala Cys Pro Ala Met Thr Glu Leu Glu Ile
            20                  25                  30

Ile Met Leu Asp Trp Leu Gly Arg Met Ile Gly Leu Pro Asp Ala Phe
```

```
                    35                  40                  45
Leu Pro Phe Thr Glu Asn Gly Lys Gly Gly Val Ile Gln Gly Ser
    50                  55                  60
Ala Ser Glu Cys Asn Phe Val Ser Leu Leu Ala Arg Phe Glu Val
65                  70                  75                  80
Leu Lys Glu Leu Lys Gln Arg Phe Pro Phe Val Glu Glu Gly Leu Leu
                85                  90                  95
Leu Ser Lys Leu Val Ala Tyr Cys Ser Lys Glu Ala His Ser Ser Val
            100                 105                 110
Glu Lys Ala Cys Met Ile Gly Met Val Lys Leu Lys Ile Leu Asp Thr
        115                 120                 125
Asp Ala Lys Phe Arg Leu Arg Gly Glu Thr Leu Arg Leu Ala Ile Glu
    130                 135                 140
Glu Asp Arg Asn Leu Gly Leu Ile Pro Phe Phe Val Ser Thr Thr Leu
145                 150                 155                 160
Gly Thr Thr Ser Cys Cys Ser Phe Asp Val Leu Ser Glu Ile Gly Pro
                165                 170                 175
Val Cys Gln Glu Asn Asp Leu Trp Leu His Val Asp Gly Ala Tyr Gly
            180                 185                 190
Gly Ser Ala Met Ile Cys Pro Glu Phe Arg Pro Leu Met Glu Gly Ile
        195                 200                 205
Glu Cys Ala Met Ser Phe Asn Thr Asn Pro Asn Lys Phe Met Leu Val
    210                 215                 220
Asn Phe Asp Cys Ser Thr Met Trp Val Lys Asp Arg Tyr Lys Leu Thr
225                 230                 235                 240
Gln Ala Leu Val Val Asp Pro Leu Tyr Leu Gln His Ser Trp Thr Asp
                245                 250                 255
Lys Ala Ile Asp Tyr Arg His Trp Ser Ile Pro Leu Ser
            260                 265
```

<210> SEQ ID NO 18
<211> LENGTH: 808
<212> TYPE: DNA
<213> ORGANISM: Dirofilaria immitis

<400> SEQUENCE: 18

```
gactaagtgg tatactccaa tgacgataat ctattgcctt gtctgtccaa ctgtgttgca    60
agtatagagg atcaacaact agagcttggg ttagcttgta gcgatctttt acccacattg   120
tagaacaatc aaaattgacg agcatgaatt tatttggatt ggtgttgaaa ctcatcgcac   180
attcgatccc ttccattagc ggtcggaatt ctgggcaaat catcgcactt cctccatacg   240
ctccatctac atgtagccat aaatcatttt cttgacaaac gggtccaatt tctgagagga   300
cgtcaaagga gcagcaggat gtggtgccaa gagtagtgga aacaaaaaac ggtattaagc   360
caagattacg atcttcctct attgccagac gtaatgtttc accacgtaaa cgaaactttg   420
catcagtgtc caaatcttc aatttaacca tgccgatcat gcaagccttc tcgactgatg   480
aatgagcttt tttagaacaa tatgcgacta attttgacag caatagtcct tcttcaacaa   540
atggaaaacg ttgtttaagc tctttgagca cttcaaatcg tgctgctaat agcgaaacaa   600
aattacattc acttgcagaa ccctgaataa caccgccacc ttttccattt tcggtgaatg   660
gcaaaaaagc atctggaagg ccaatcattc gaccaagcca atccagcata attatttcta   720
attcagtcat tgcaggacat gcggcccaag aaaagccaac tgcaccaata gcatctgaaa   780
tcatatcagc caaaatattc ggaaaagc                                      808
```

<210> SEQ ID NO 19
<211> LENGTH: 549
<212> TYPE: DNA
<213> ORGANISM: Brugia malayi
<220> FEATURE:
<221> NAME/KEY: CDS
<222> LOCATION: (1)..(549)

<400> SEQUENCE: 19

```
gcc ttt ccg aat ctt ttg gct gat atg att tca gat gcc atc ggt gca    48
Ala Phe Pro Asn Leu Leu Ala Asp Met Ile Ser Asp Ala Ile Gly Ala
  1               5                  10                  15 gtt ggc ttt tcc tgg gcg gcg tgt cct gcg atg aca gag cta gaa ata    96
Val Gly Phe Ser Trp Ala Ala Cys Pro Ala Met Thr Glu Leu Glu Ile
             20                  25                  30 atc atg ttg gat tgg ttt ggt cga atg atc ggt ttg cca gat gct ttt   144
Ile Met Leu Asp Trp Phe Gly Arg Met Ile Gly Leu Pro Asp Ala Phe
         35                  40                  45 ttg cca ttt acc gaa aac gga aaa ggt ggc ggt gtc ata cag ggt tcc   192
Leu Pro Phe Thr Glu Asn Gly Lys Gly Gly Gly Val Ile Gln Gly Ser
     50                  55                  60 gca agt gaa tgc aat ttt gtt tcg tta cta gca gca cga ttt gaa gtg   240
Ala Ser Glu Cys Asn Phe Val Ser Leu Leu Ala Ala Arg Phe Glu Val
 65                  70                  75                  80 ctt aaa gag ctt agg caa cgt ttt cca ttt gtg gaa gaa gga ctt tta   288
Leu Lys Glu Leu Arg Gln Arg Phe Pro Phe Val Glu Glu Gly Leu Leu
                 85                  90                  95 ctg tca aaa tta gtc gca tac tgt tct aaa gaa gct cat tca tca gtc   336
Leu Ser Lys Leu Val Ala Tyr Cys Ser Lys Glu Ala His Ser Ser Val
            100                 105                 110 gag aaa gct tgc atg atc ggg atg gtc aag ttg aaa att ttg gat act   384
Glu Lys Ala Cys Met Ile Gly Met Val Lys Leu Lys Ile Leu Asp Thr
        115                 120                 125 gac aca aag ttt cgt tta cgc ggc aaa aca cta cgt tta gcg ata gag   432
Asp Thr Lys Phe Arg Leu Arg Gly Lys Thr Leu Arg Leu Ala Ile Glu
    130                 135                 140 gaa gat cgt aat ctt ggc tta ata cca ttt ttc gtt tct act acc ctt   480
Glu Asp Arg Asn Leu Gly Leu Ile Pro Phe Phe Val Ser Thr Thr Leu
145                 150                 155                 160 ggc aca aca tct tgc tgc tcg ttc gat gtt ctc tcc gaa att ggt cct   528
Gly Thr Thr Ser Cys Cys Ser Phe Asp Val Leu Ser Glu Ile Gly Pro
                165                 170                 175 gtc tgt cat gaa aat gat tta                                       549
Val Cys His Glu Asn Asp Leu
            180
```

<210> SEQ ID NO 20
<211> LENGTH: 183
<212> TYPE: PRT
<213> ORGANISM: Brugia malayi

<400> SEQUENCE: 20

```
Ala Phe Pro Asn Leu Leu Ala Asp Met Ile Ser Asp Ala Ile Gly Ala
  1               5                  10                  15

Val Gly Phe Ser Trp Ala Ala Cys Pro Ala Met Thr Glu Leu Glu Ile
             20                  25                  30

Ile Met Leu Asp Trp Phe Gly Arg Met Ile Gly Leu Pro Asp Ala Phe
         35                  40                  45

Leu Pro Phe Thr Glu Asn Gly Lys Gly Gly Gly Val Ile Gln Gly Ser
     50                  55                  60
```

```
Ala Ser Glu Cys Asn Phe Val Ser Leu Leu Ala Ala Arg Phe Glu Val
 65                  70                  75                  80

Leu Lys Glu Leu Arg Gln Arg Phe Pro Phe Val Glu Glu Gly Leu Leu
                 85                  90                  95

Leu Ser Lys Leu Val Ala Tyr Cys Ser Lys Glu Ala His Ser Ser Val
            100                 105                 110

Glu Lys Ala Cys Met Ile Gly Met Val Lys Leu Lys Ile Leu Asp Thr
            115                 120                 125

Asp Thr Lys Phe Arg Leu Arg Gly Lys Thr Leu Arg Leu Ala Ile Glu
            130                 135                 140

Glu Asp Arg Asn Leu Gly Leu Ile Pro Phe Phe Val Ser Thr Thr Leu
145                 150                 155                 160

Gly Thr Thr Ser Cys Cys Ser Phe Asp Val Leu Ser Glu Ile Gly Pro
                165                 170                 175

Val Cys His Glu Asn Asp Leu
            180

<210> SEQ ID NO 21
<211> LENGTH: 549
<212> TYPE: DNA
<213> ORGANISM: Brugia malayi

<400> SEQUENCE: 21
taaatcattt tcatgacaga caggaccaat ttcggagaga acatcgaacg agcagcaaga    60
tgttgtgcca agggtagtag aaacgaaaaa tggtattaag ccaagattac gatcttcctc   120
tatcgctaaa cgtagtgttt tgccgcgtaa acgaaacttt gtgtcagtat ccaaaatttt   180
caacttgacc atcccgatca tgcaagcttt ctcgactgat gaatgagctt ctttagaaca   240
gtatgcgact aattttgaca gtaaaagtcc ttcttccaca aatggaaaac gttgcctaag   300
ctctttaagc acttcaaatc gtgctgctag taacgaaaca aaattgcatt cacttgcgga   360
accctgtatg acaccgccac cttttccgtt ttcggtaaat ggcaaaaaag catctggcaa   420
accgatcatt cgaccaaacc aatccaacat gattatttct agctctgtca tcgcaggaca   480
cgccgcccag gaaaagccaa ctgcaccgat ggcatctgaa atcatatcag ccaaaagatt   540
cggaaaggc                                                          549

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 22
tgggcngcnt gyccngcnat gacngarctn gar                                33
```